United States Patent
Treas

(10) Patent No.: US 8,541,756 B1
(45) Date of Patent: Sep. 24, 2013

(54) SYSTEMS AND METHODS FOR GENERATING X-RAYS AND NEUTRONS USING A SINGLE LINEAR ACCELERATOR

(75) Inventor: Paul Dennis Treas, Livermore, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

(21) Appl. No.: 13/466,521

(22) Filed: May 8, 2012

(51) Int. Cl.
| H01J 1/50 | (2006.01) |
| G01T 3/00 | (2006.01) |
| G01T 1/00 | (2006.01) |

(52) U.S. Cl.
USPC ...... 250/398; 250/390.01; 250/391; 250/393; 250/396 R; 378/143

(58) Field of Classification Search
USPC .................. 250/306, 370.01, 370.04, 370.09, 250/390.01, 391, 393, 396 R, 398; 378/57, 378/62, 143
See application file for complete search history.

(56) References Cited

U.S. PATENT DOCUMENTS

| 4,251,726 A * | 2/1981 | Alvarez | 376/159 |
| 5,838,759 A | 11/1998 | Armistead | |
| 6,444,990 B1 | 9/2002 | Morgan et al. | |
| 7,399,976 B2 | 7/2008 | Kang et al. | |
| 7,453,987 B1 | 11/2008 | Richardson | |
| 7,551,714 B2 | 6/2009 | Rothschild | |
| 7,809,103 B2 | 10/2010 | Du et al. | |
| 7,835,499 B2 | 11/2010 | Yu et al. | |
| 8,098,796 B2 | 1/2012 | Schumacher et al. | |
| 8,106,365 B2 | 1/2012 | Perticone et al. | |
| 2007/0096036 A1* | 5/2007 | Kang et al. | 250/390.04 |
| 2007/0286339 A1* | 12/2007 | Rothschild | 378/57 |
| 2009/0225931 A1* | 9/2009 | Rothschild | 378/6 |
| 2010/0127169 A1 | 5/2010 | Whittum et al. | |
| 2010/0195791 A1 | 8/2010 | Ishkhanov et al. | |
| 2011/0206179 A1 | 8/2011 | Bendahan | |

* cited by examiner

*Primary Examiner* — Mark R Gaworecki
(74) *Attorney, Agent, or Firm* — Lowenstein Sandler LLP

(57) ABSTRACT

Systems and methods for generating X-rays and neutrons using a single linear accelerator are disclosed. Such system and methods may interrogate an object at times with X-rays and at other times with neutrons, e.g., after suspicious material is detected based on the X-rays. A system may include a single linear accelerator for generating first and second electron beams; first and second targets; a magnet configured to control irradiation of the first and second targets by the first and second electron beams; and a controller that (a) causes the linear accelerator to generate the first electron beam and causes the magnet to direct the beam to first target to generate X-rays; and (b) causes the linear accelerator to generate the second electron beam and causes the magnet to direct the beam to the second target to generate neutrons.

26 Claims, 15 Drawing Sheets

SYSTEMS AND METHODS FOR GENERATING X-RAYS AND NEUTRONS USING A SINGLE LINEAR ACCELERATOR

FIELD OF THE INVENTION

This application generally relates to generating X-rays and neutrons, for example to interrogate cargo containers for potentially dangerous materials.

BACKGROUND OF THE INVENTION

Cargo containers are typically used to transport goods internationally and domestically. Large numbers of such containers are loaded and unloaded at ports on an ongoing basis. Due to the large number of containers, port inspectors may not be able to open the containers to inspect their contents. This can pose a security risk.

To address the security risk introduced by an inability to open and inspect the contents of cargo containers, cargo inspection devices have been developed that scan the interiors of the containers without requiring inspectors to open the containers. Some cargo inspection devices perform radioscopic examination of cargo containers using an X-ray beam or gamma beam that can penetrate the container to identify its contents, for example by transmitting the beam through the container. A detector receives X-rays that have penetrated the shipping container without being absorbed or scattered, and produces an image of the contents of the shipping container. The image can be displayed to an inspector who can perform visual inspection of the contents. Materials with higher effective atomic number (Z) have a higher density, thus resulting in greater attenuation of the beam. Portions of the image showing greater X-ray attenuation may alert the inspector to the presence of a high-Z material for which further inspection is appropriate, e.g., a radioactive material.

Some X-ray based cargo inspection devices generate X-rays using a linear accelerator configured to produce a single energy X-ray beam. However, one shortcoming of such a single energy system is that it may not be possible to uniquely determine whether the X-rays are attenuated by a material that has a particularly high Z, or whether the material simply is very thick, both of which may cause similar attenuation of the X-rays. Other cargo inspection devices use dual energy linear accelerators that are configured to emit two different energy level X-ray beams. With a dual energy X-ray inspection system, materials can be discriminated radiographically by alternately irradiating an object with X-ray beams of two different energies. Dual energy X-ray inspection systems can determine a material's mass absorption coefficient, and therefore the material's Z. Differentiation is achieved by comparing the attenuation ratio obtained from irradiating the container with low-energy X-rays to the attenuation ratio obtained from irradiating the container with high-energy X-rays. Discrimination is possible because different materials have different degrees of attenuation for high-energy X-rays and low-energy X-rays, and that allows identification of low-Z-number materials (such as but not limited to organic materials), medium-Z-number materials (such as but not limited to transition metals), and high-Z-number materials (such as but not limited to radioactive materials) in the container. Such systems therefore may provide an image of the cargo contents and identify the materials within the container.

The ability of dual energy X-ray inspection systems to detect the Z number of materials being scanned enables such inspection systems to automatically detect the different materials in a container, including radioactive materials and contraband such as but not limited to cocaine and marijuana. However, previously known dual energy X-ray inspection systems use a standing wave linear accelerator that is vulnerable to frequency and power jitter and temperature fluctuations, causing the beam energy from the linear accelerator to be unstable when operated to accelerate electrons to a low energy. The energy jitter and fluctuations may create image artifacts, which cause an improper Z number of a scanned material to be identified. This may cause false positives (in which a targeted material is identified even though no targeted material is present) and false negatives (in which a targeted material is not identified even though targeted material is present).

Moreover, although previously known X-ray based inspection systems may allow for some degree of material discrimination, particularly high-Z materials may require additional inspection to determine whether the materials are radioactive or otherwise dangerous. Such inspection may be performed manually by the inspector, which may be time consuming and dangerous. Alternatively, a cargo container with a particularly high-Z material may be interrogated using neutrons so as to enhance identification of the material. For example, such neutrons may generate gamma rays when they interact with a material. The gamma rays may be detected with an appropriate detector, the output of which may be analyzed to identify the materials based on the spectral characteristics of the gamma rays. Or, for example, such neutrons may generate detectable fission neutrons if they interact with a radioactive material. However, previously known neutron generators are typically relatively expensive, and so any given cargo inspection facility may have only a single such generator available, and the container may need to be physically be moved near the generator, which again may be time consuming and dangerous.

Some effort has been made to simplify the process by which cargo containers may be scanned both with X-rays and with neutrons. For example, U.S. Pat. No. 7,551,714 to Rothschild discloses a combined X-ray computerized tomography (CT) and neutron material identification system. The system includes an X-ray CT system, e.g., an X-ray tube, linear accelerator, or radioactive source, to scan a rotating cargo container with a horizontal fan beam of X-rays. An array of detectors on the other side of the container generates a three-dimensional image of the interior of the container, and any suspect regions are identified. Then, a separate neutron system, e.g., a sealed deuterium-tritium (DT) tube or high-intensity plasma neutron source, irradiates specified portions of the container with a horizontal collimated beam of high-energy neutrons. Rothschild discloses that gamma rays emitted from the suspect region are detected by energy-resolving detectors, and that the energy spectrum is analyzed and compared to a library of energy spectra of threat items found in a database. Rothschild discloses that the X-ray CT scan can be performed using dual-energy CT, resulting in a reduced number of suspect regions that will need to be interrogated by the neutron system. However, Rothschild's proposed system is cumbersome because it requires rotation of the cargo container and separately controlled X-ray and neutron systems.

U.S. Pat. No. 5,838,759 to Armistead discloses a system that uses a single beam for a combination of X-ray inspection and neutron-induced gamma-ray spectroscopy employing a "photoneutron probe." The system uses a commercial linear accelerator X-ray source to scan a cargo container to obtain an X-ray image. If nothing unusual is detected, the object is cleared. However, if suspicious shapes, densities, or compartments are revealed, the X-ray source is temporarily converted into a neutron source by causing an actuator to insert a beryllium (Be) sheet, i.e., a beam converter, into the X-ray beam, and moving the container or the detector so as to irradiate the suspicious region with neutrons. Contraband, if present, would absorb neutrons and emit gamma rays and/or fission neutrons that may be used to characterize the scanned materials. Although the same X-ray source may be used to generate both X-rays and neutrons, making the system somewhat less cumbersome than the system proposed by Rothschild, the mechanical aspects of Armistad's proposed system will necessarily increase the amount of time required to fully analyze a cargo container.

SUMMARY OF THE INVENTION

Embodiments of the present invention provide systems and methods for interleaving X-rays and neutrons using a single linear accelerator. Such a systems and methods may be used, for example, to interrogate and examine objects with a significantly higher level of precision than with solely X-rays or solely neutrons, significantly greater efficiency than a system requiring mechanical interposition of a neutron target into the X-ray beam, and with significantly less cost than a system having separate X-ray and neutron-generating sources. In particular, the systems and methods of the present invention may be used to interrogate an object with interleaved multi-energy X-rays at selected times, as well as to interrogate the same object with neutrons at other selected times, e.g., after a suspicious material is detected based on the X-rays. The systems may convert between interrogating the object with X-rays and neutrons without requiring mechanical movement of the system or the object, but instead by actuating a magnet so as to selectably direct a beam of electrons generated by the linear accelerator between an X-ray target that generates X-rays when irradiated with an electron beam, and a neutron target that generates neutrons when irradiated with an electron beam. The linear accelerator may be controlled to select the energy of the electron beam so as to enhance the efficiency with which the particular particles are generated, and also may be controlled to select the pulse width or beam current of the electron beam so as to select the dose of the particular particles generated. As such, the system may readily be switched back and forth between generating neutrons and X-rays at desired doses so as to irradiate the same object with different types of particles, at known doses, and thus to obtain greatly enhanced information about the object, without the added cost of a previously-known neutron source or the need to move the object, the system, or any mechanical component therein so as to interrogate the object.

Under one aspect, a system for interrogating an object includes a single linear accelerator configured to generate first and second electron beams respectively having first and second energies; first and second targets; and a magnet configured to control irradiation of the first and second targets by the first and second electron beams. The system also includes a controller in operable communication with the linear accelerator and with the magnet. The controller is configured to (a) cause the linear accelerator to generate the first electron beam at a first time and cause the magnet to direct the first electron beam to the first target so as to generate a first X-ray beam that has a first X-ray energy and irradiates the object; and (b) cause the linear accelerator to generate the second electron beam at a second time and cause the magnet to direct the second electron beam to the second target so as to generate a neutron beam that irradiates the object.

In some embodiments, the magnet is configured to deflect the second electron beam to irradiate the second target responsive to a control signal from the controller. The magnet also may be configured to allow the first electron beam to irradiate the first target without deflection responsive to a control signal from the controller.

In some embodiments, the controller is configured to interleave the first X-ray beam and the neutron beam by repeating (a) and (b).

Some embodiments include an X-ray detector configured to detect a percent transmission of the first X-ray beam through the object. The controller may be in operable communication with the detector, and configured to perform (b) when the percent transmission is less than a predetermined threshold.

In some embodiments, the linear accelerator is further configured to generate a third electron beam having a third energy. The controller may be further configured to (c) cause the linear accelerator to generate the third electron beam at a third time and cause the magnet to direct the third electron beam to the first target so as to generate a second X-ray beam that has a second X-ray energy and irradiates the object. The controller may be configured to interleave the first and second X-ray beams and the neutron beam by repeating (a), (b), and (c). The system may include an X-ray detector configured to detect percent transmissions of the first and second X-ray beams through the object. The controller may be in operable communication with the detector and configured to perform (b) when the percent transmissions are less than a predetermined threshold.

In an illustrative embodiment, the linear accelerator and the first and second targets all share a common vacuum.

The controller may be further configured to select a dose of the first X-ray beam by selecting one of a beam current and a pulse width of the first electron beam, and to select a dose of the neutron beam by selecting one of a beam current and a pulse width of the second electron beam.

The first and second energies of the first and second electron beams may be different from one another.

Under another aspect, a method of interrogating an object includes: generating with a single linear accelerator first and second electron beams respectively having first and second energies; directing the first electron beam to a first target so as to generate a first X-ray beam having a first X-ray energy at a first time; irradiating the object with the first X-ray beam; directing the second electron beam to a second target so as to generate a neutron beam at a second time; and irradiating the object with the neutron beam.

DETAILED DESCRIPTION

Embodiments of the present invention provide systems and methods that interleave X-rays and neutrons using a single linear accelerator. Specifically, the X-rays and neutrons may be generated at different times from one another and in an automated fashion so as to quickly and sufficiently interrogate an object (e.g., a closed cargo container) to determine whether the container may contain dangerous materials. For example, the single linear accelerator may sequentially generate two or more electron beams having different energies than one another. The first electron beam may be directed to a first target, where the beam generates X-rays that irradiate the object. The second electron beam may be directed to a second target, where the beam generates neutrons that irradiate the object. A magnet may be used to direct the electron beams to their respective targets on a pulse-by-pulse basis, enabling rapid switching between X-ray and neutron generation. As such, if the object appears to contain a suspicious material based on the X-rays, the system may immediately switch to generating neutrons to further interrogate the object, and subsequently switch back to generating X-rays for interrogating other objects. Preferably, the system is configured to generate multi-energy X-rays so as to improve X-ray interrogation of the object.

First, an overview of the systems and methods will be provided. Then, further detail on a linear accelerator that is particularly well suited for use with the systems and methods will be described.

Figure 1:
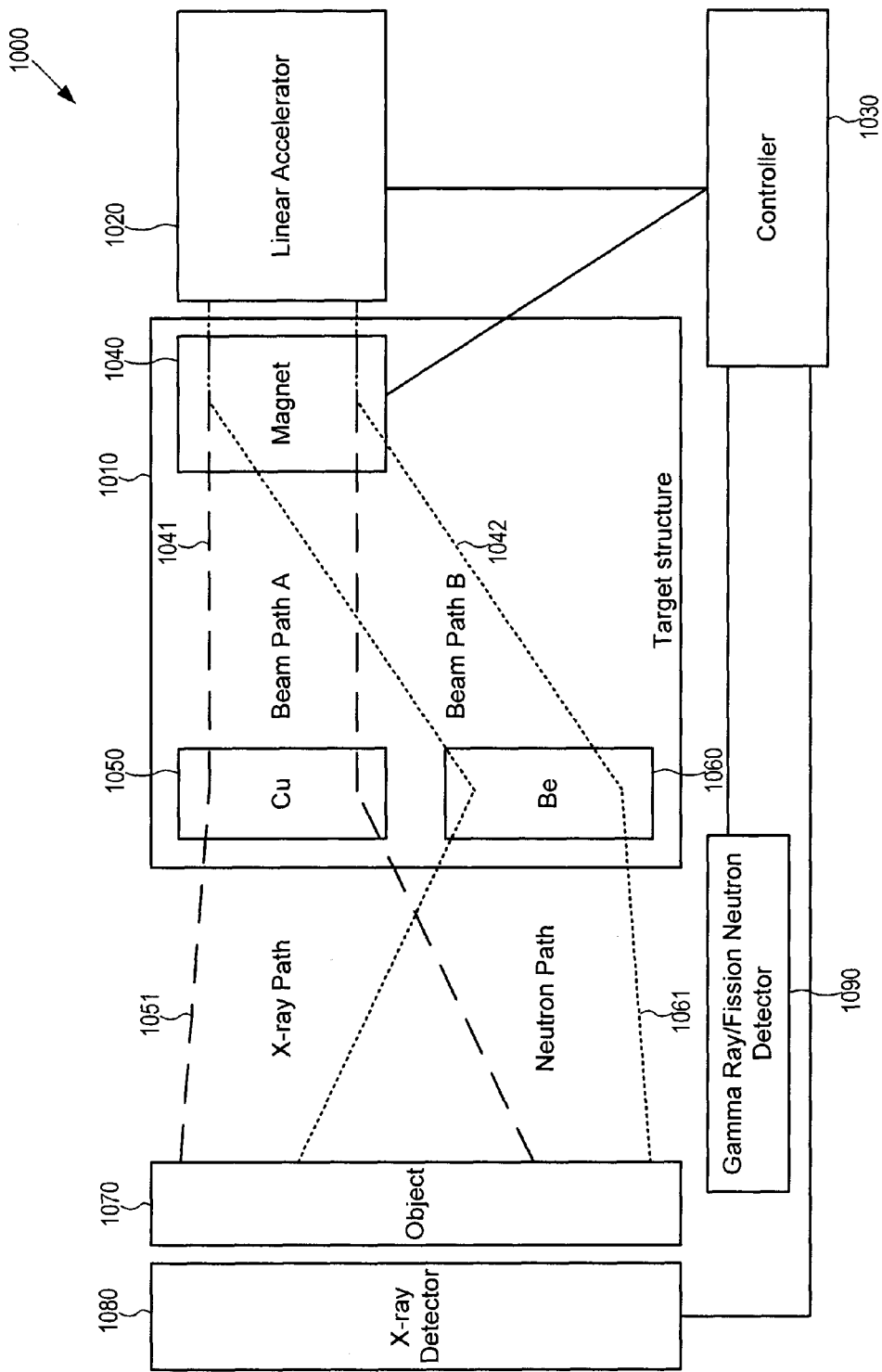
FIG. 1 illustrates a block diagram of a system for generating X-rays and neutrons using a single linear accelerator, according to some embodiments of the present invention.

FIG. 1 schematically illustrates a block diagram of system 1000 for interrogating object 1070. System 1000 includes target structure 1010 configured to receive electrons from a single linear accelerator 1020. Target structure 1010 includes magnet 1040, first target 1050, and second target 1060 which may be arranged relative to a common vacuum envelope and shielding such as described in further detail below with reference to FIG. 5. System 1000 is operably coupled to, and configured to receive signals from, X-ray detector 1080 and gamma ray/fission neutron detector 1090. System 1000 also includes controller 1030, which is in operable communication with linear accelerator 1020, magnet 1040, X-ray detector 1080, and gamma ray/fission neutron detector 1090. Controller 1030 sends control signals to linear accelerator 1020 and magnet 1040 that cause electron beams of different energies to be generated and respectively directed along beam paths 1041, 1042 so as to respectively irradiate the first and second targets 1050, 1060 and thus respectively generate X-rays 1051 and neutrons 1061 for irradiating object 1070, as described in greater detail below with reference to FIG. 2A. Additionally, system 1000 may generate multi-energy X-rays so as to provide enhanced interrogation of object 1070, as described in greater detail below with reference to FIG. 2B. Optionally, controller 1030 controls linear accelerator 1020 and magnet 1040 based on measurements of X-ray transmission through object 1070 made by X-ray detector 1080 and/or by measurements of neutron emission by object 1070 made by gamma ray/fission neutron detector 1090, as described in greater detail below with reference to FIG. 2C. Note that each of single linear accelerator 1020, X-ray detector 1080, and/or gamma ray/fission neutron detector 1090 may be, but need not necessarily be, considered part of system 1000. That is, system 1000 may be used with existing accelerators, X-ray detectors, and gamma ray or fission neutron detectors; optionally, all of these components may be considered together as constituting a single system. An exemplary linear accelerator that is particularly well suited for use with system 1000, and optionally may be considered to be part of system 1000, is described herein.

Linear accelerator 1020 may be a travelling wave (TW) or standing wave (SW) linear accelerator configured for interleaved multi-energy operation. That is, linear accelerator 1020 is configured to generate electron beams of different energies at different times. Such a configuration facilitates efficient generation of X-rays and neutrons, respectively, because the energy of the electron beam may be selected to improve yield of the particles to be generated. For example, a first electron beam may be directed along beam path A (1041) so as to irradiate first target 1050, which may be copper (Cu), and which generates X-rays having a selected X-ray energy responsive to the irradiation. A second electron beam may be directed along beam path B (1042) so as to irradiate second target 1060, which may be beryllium (Be), and which generates neutrons of a selected energy responsive to the irradiation. The efficiency with which the first electron beam is converted to X-rays and the energy of the X-rays, as well as the efficiency with which the second electron beam is converted to neutrons and the energy of the neutrons, is based respectively on the energies of the first and second electron beams. Controller 1030 preferably sends appropriate signals to linear accelerator 1020 to cause the accelerator to adjust the energies of the first and second electron beams to respectively enhance efficiency of X-ray and neutron generation based on the materials used in the first and second targets, respectively. Additionally, as described in greater detail below with reference to FIG. 2B, linear accelerator 1020 may configured to generate electron beams of three or more different energies, which may be used to generate multi-energy X-rays as well as neutrons.

Magnet 1040 may be positioned between linear accelerator 1020 and first and second targets 1050, 1060, and configured to direct an electron beam either to first target 1050 or to second target 1060 by applying a magnetic field to the electron beam responsive to appropriate control signals from controller 1030. For example, in the illustrated embodiment, magnet 1040 is configured such that a first electron beam may travel undeflected along beam path A (1041) between linear accelerator 1020 and first target 1050. Such lack of deflection of the first electron beam may be responsive to a first control signal from controller 1030 to magnet 1040, or may simply be a "default" position in which magnet 1040 is not actuated and a control signal is not required. Magnet 140 also may be configured so as to magnetically deflect a second electron beam along beam path B (1042) between linear accelerator 1020 and second target 1060 responsive to an appropriate control signal from controller 1030. Such an arrangement may be useful because system 1000 may primarily generate X-rays to initially interrogate objects, and may only occasionally generate neutrons to more thoroughly interrogate objects. Because magnet 1040 need not actively deflect the electron beam onto beam path A (1041) so as to irradiate first target 1050, but only to deflect the electron beam onto beam path B (1042) to irradiate second target 1060, the amount of energy required to operate the system may be reduced. Note that because the state of magnet 1040 determines the direction in which the electron beam travels, magnet 1040 is considered to "direct" the electron beams onto both paths A and B even if the magnet does not actively deflect the beams onto both paths. In alternative embodiments, magnet 1040 instead may be actuated only to deflect the electron beam onto path B, or instead may be actuated to deflect the electron beam onto both paths A and B.

In some embodiments, magnet 1040 is a "kicker" magnet operable to deflect the second beam of electrons to the second target on a pulse-by-pulse basis. For example, kicker magnet 1040 may be configured so as to direct a single electron beam to first target 1050, then to direct the temporally next electron beam to second target 1060, and then to direct the temporally next electron beam to first target 1050, and so on. Other temporal deflection patterns are possible. For example, kicker magnet 1040 may individually direct only occasional electron beams to second target 1060, such as if the percent transmission of X-rays through object 1070 is sufficiently low as to warrant further investigation with neutrons, such as described below with reference to FIG. 2C. In alternative embodiments, magnet 1040 is a "DC" magnet operable to deflect electron beams to the second target on a relatively long time frame, rather than on a pulse-by-pulse basis, as a result of the relatively slow ability of DC magnets to magnetically deflect electron beams.

Controller 1030 may coordinate the operation of linear accelerator 1020 and magnet 1040, so as to synchronize the linear accelerator's generation of electron beams having selected energies with the magnet's direction of those beams to the appropriate target. For example, controller 1030 may be configured to send one or more signals to linear accelerator 1020 and magnet 1040, respectively, at different times. One signal may cause linear accelerator 1020 to generate a first electron beam having a first energy, at a first time. Another signal may cause magnet 1040 to direct the first electron beam onto beam path A (1041) synchronously with the generation of that electron beam; alternatively, as discussed above, magnet 1040 may as a default position allow the first electron beam to travel onto beam path A (1041) without requiring active deflection of the beam (the magnet still being considered to "direct" the beam onto path A even without actively deflecting the beam). At a later time, controller 1030 may generate other signals, one of which may cause linear accelerator 1020 to generate a second electron beam having a second energy, at a second time, and another of which may cause magnet 1040 to direct the second electron beam onto beam path B (1042) synchronously with the generation of that electron beam. As such, controller 1030 causes linear accelerator 1020 and magnet 1040 to work in synchrony with one another so as to generate X-rays and neutrons at different times from one another. As described in greater detail below with reference to FIGS. 2A-2C, controller 1030 may be configured to repeat this process so as to interleave the X-ray and neutron beams, and/or may be configured to cause the neutron beam to be generated responsive to measurements of the percent transmission of the X-rays through object 1070.

Additionally, in embodiments where linear accelerator 1020 is a TW linear accelerator such as described further below with reference to FIGS. 4-13, controller 1030 may be configured to adjust the dose of the X-ray and/or neutron beam by selecting the pulse width and/or beam current of the electron beams generated by linear accelerator 1020, for example by sending appropriate control signals to the linear accelerator. For further information on adjusting doses based on pulse width and/or beam current, see commonly owned U.S. patent application Ser. No. 12/976,810, entitled "Traveling Wave Linear Accelerator Based X-ray Source Using Current to Modulate Pulse-to-Pulse Dosage," and U.S. patent application Ser. No. 12/976,787, entitled "Traveling Wave Linear Accelerator Based X-ray Source Using Pulse Width to Modulate Pulse-to-Pulse Dosage," the entire contents of both of which are incorporated by reference herein.

Note although linear accelerator 1020 preferably is configured to generate electron beams having different energies than one another, electron beams having the same energies as one another also may suitably be used to generate X-rays and neutrons using the same linear accelerator, although the efficiency of the X-ray and neutron generation may not individually be optimized. Instead, the central energy of the electron beam may be selected so as to provide an overall efficiency of X-ray and neutron generation that is satisfactory. Magnet 1040 may direct the electron beam onto beam paths A and B (1041, 1042) at appropriate times, analogously as described above for the multiple-energy embodiment.

First target 1050 may include any material that generates a sufficient quantity of X-rays when irradiated with an electron beam of appropriate energy, including tungsten, certain tungsten alloys (such as but not limited to tungsten carbide, or tungsten (95%)-rhenium (5%)), molybdenum, copper, platinum and cobalt. In the illustrated embodiment, target 1050 is copper. Further detail on target 1050 is provided further below with reference to FIG. 5. When irradiated with an electron beam of appropriate energy, target 1050 generates X-rays that irradiate object 1070 along X-ray path 1051. Note that the particular trajectory of path 1051 is purely illustrative and not drawn to scale, and will depend upon the beam characteristics of the first electron beam, on the properties of target 1050, and the distance between target 1050 and object 1070, among other factors, as will be appreciated by those skilled in the art.

Second target 1060 may include any material that generates a sufficient quantity of neutrons when irradiated with an electron beam of appropriate energy, including beryllium, tantalum, depleted uranium, tungsten, or lead. Optionally, second target 1060 may include a stack of two or more separate targets in series with one another, where each target may be formed of a material that is the same as, or different than, other targets in the stack. Such a configuration may provide enhanced selectivity in producing certain types or energies of neutrons and/or enhanced neutron flux. In either embodiment, when irradiated with an electron beam of appropriate energy, target 1060 generates neutrons that irradiate object 1070 along neutron path 1052. Note that the particular trajectory of path 1052 is purely illustrative and not drawn to scale, and will depend upon the beam characteristics of the second electron beam, on the properties of target 1060, and the distance between target 1060 and object 1070, among other factors, as will be appreciated by those skilled in the art.

X-ray detector 1080 and gamma ray/fission neutron detector 1090 may have any suitable construction known in the art, are in operable communication with controller 1030, and are respectively configured to detect X-rays transmitted through, and gamma rays or fission neutrons generated by, object 1070 responsive to irradiation of the object with X-rays and neutrons, respectively.

Methods of using system 1000 illustrated in FIG. 1 to interrogate objects will now be described with reference to FIGS. 2A-2C and 3A-3C.

Figure 2A:
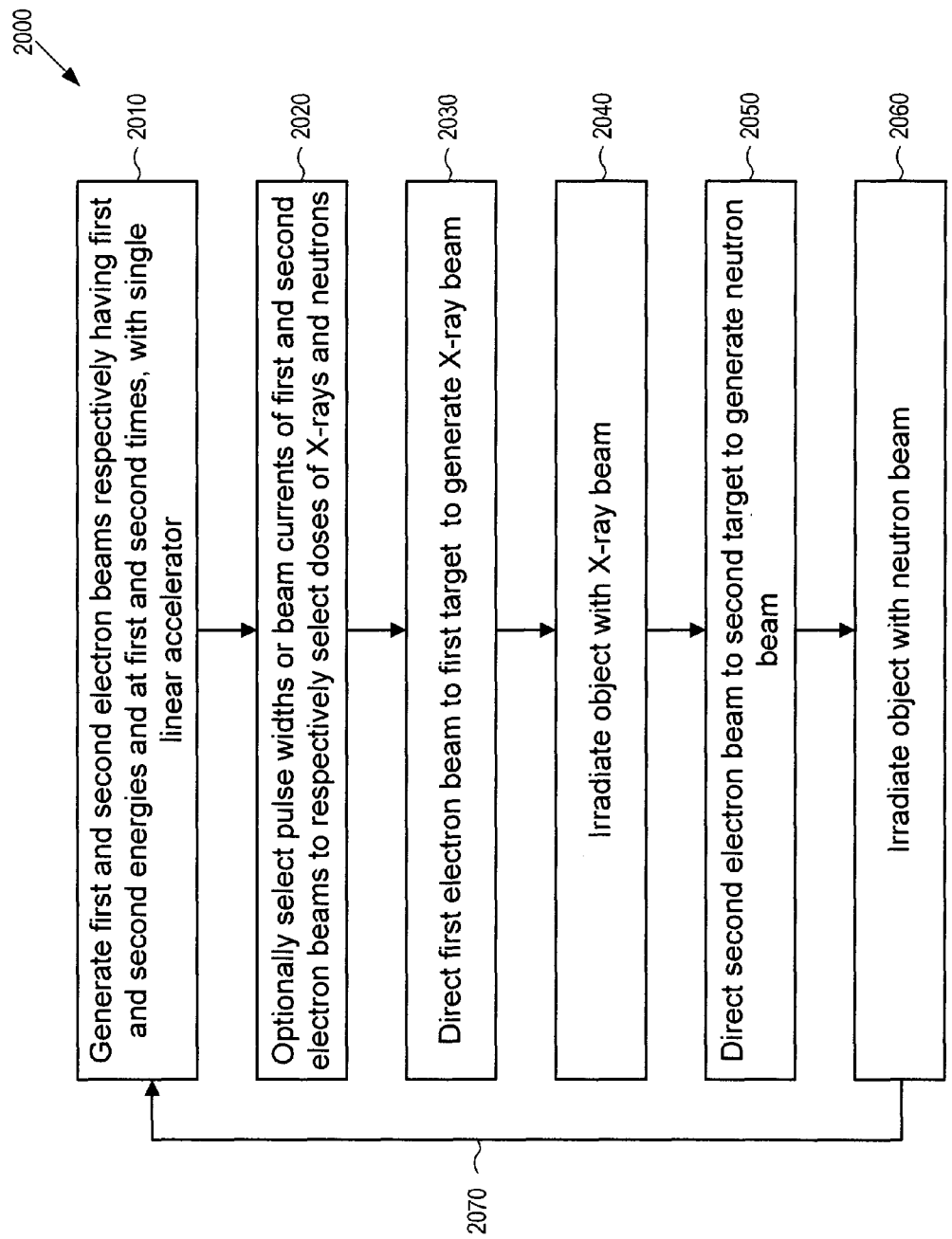
FIG. 2A illustrates steps in a method for generating X-rays and neutrons using a single linear accelerator, according to some embodiments of the present invention.

FIG. 2A illustrates a method 2000 of interrogating an object using X-rays and neutrons generated by a single linear accelerator, e.g., using system 1000. Method 2000 includes generating first and second electron beams having first and second energies, and at first and second times, respectively, with a single linear accelerator (step 2010). For example, as described above with reference to FIG. 1, linear accelerator 1020 may generate such first and second electron beams at different times and with different energies responsive to signals from controller 1030.

Method 2000 illustrated in FIG. 2A optionally includes selecting the pulse widths and/or beam currents of the first and second electron beams, so as to respectively select doses of the X-rays and neutrons (step 2020). Such dose selection may be useful in tailoring the beams to the particular application at hand, e.g., to ensure that the object is sufficiently irradiated to obtain useful information about the object, while avoiding saturation of the X-ray and neutron detectors and reducing the operator's exposure to radiation.

Method 2000 includes directing the first electron beam to a first target to generate an X-ray beam (step 2030). The object is irradiated with the X-ray beam (step 2040). The second electron beam is directed to the second target to generate a neutron beam (step 2050). The object is irradiated with the neutron beam (step 2060).

Figure 3A:
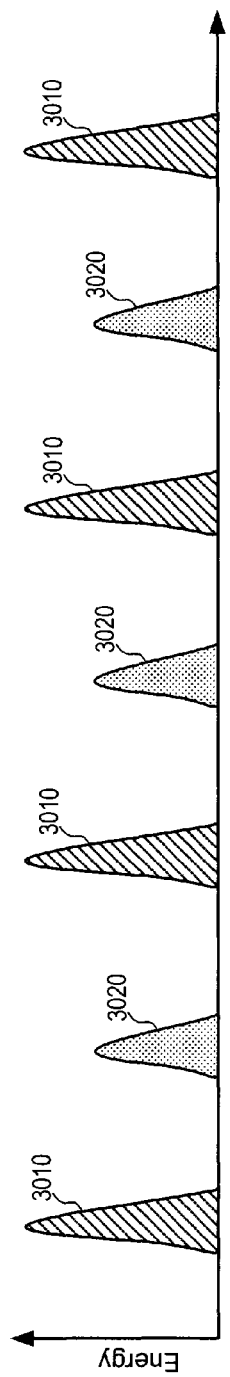
FIGS. 3A-3C illustrate exemplary sequences of electron pulses, X-rays, and neutrons that may be generated using the system of FIG. 1 during the methods of FIGS. 2A-2C.

Optionally, steps 2010 through 2060 may be repeated so as to interleave generation of X-rays with generation of neutrons with a predetermined frequency, as represented by arrow 2070 of FIG. 2A. For example, FIG. 3A illustrates a sequence of X-ray pulses 3010 that are interleaved with neutron pulses 3020 on a one-to-one basis. Other interleaving sequences are possible, e.g., several X-ray pulses followed by one or a few neutron pulses, followed by several X-ray pulses, and so on. Additionally, note that the energies of the X-rays and neutrons are not to scale with one another, and each particle type may have any selected energy and/or dose.

Figure 2B:
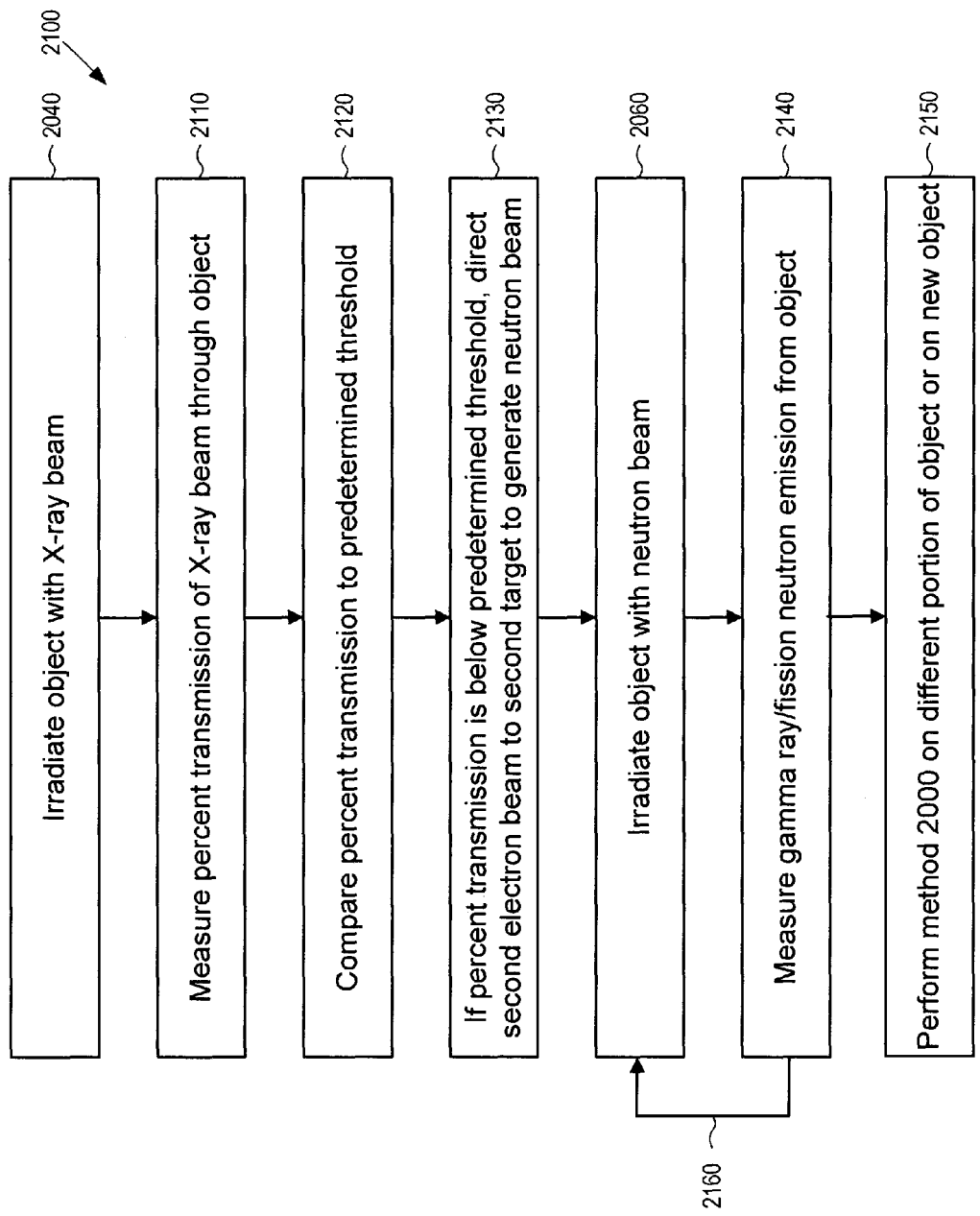
FIG. 2B illustrates an enhancement of the method of FIG. 2A in which the neutrons are generated responsive to the measured percent transmission of the X-rays through an object.
Figure 2C:
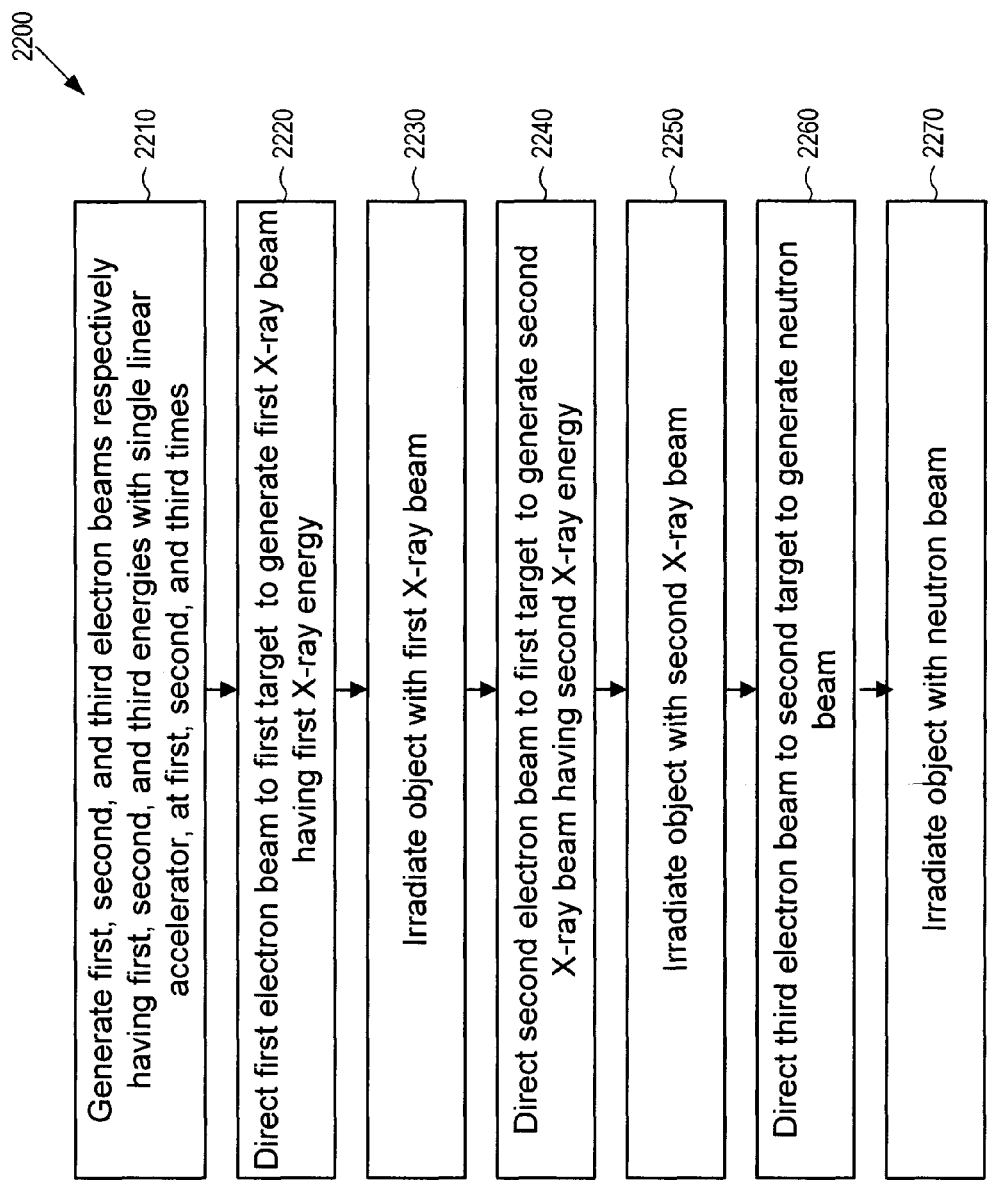
FIG. 2C illustrates steps in a method for generating multi-energy X-rays and neutrons using a single linear accelerator, according to some embodiments of the present invention.

Alternatively, in method 2100 illustrated in FIG. 2B, the controller may use the percent transmission of the X-rays through the object as a basis for generating neutrons by deflecting the electron beam to the second target. Note that although the neutrons may be generated only occasionally and/or at irregular intervals, they still may be considered to be "interleaved" with the X-rays because the system may alternately generate neutrons and X-rays at desired times.

Method 2100 begins when the object is irradiated with the X-ray beam (step 2040 of FIG. 2A). The percent transmission of the X-ray beam through the object may be measured (step 2110), for example using X-ray detector 1080 illustrated in FIG. 1. For example, controller 1030 may be configured to receive an output signal from X-ray detector 1080 based on the magnitude of X-ray transmission through object 1070. Controller 1030 also may be configured to receive an output signal from X-ray intensity monitor 31 described further below with reference to FIG. 5. Based on the signals from X-ray detector 1080 and intensity monitor 31, controller 1030 may determine the percent transmission of X-rays through the object. Other methods of determining the percent transmission suitably may be used.

Referring again to FIG. 2B, the percent transmission of the X-rays then may be compared to a predetermined threshold (step 2120). The predetermined threshold may represent a percent transmission below which an object may be considered to be "suspicious," e.g., having a particularly high Z that strongly absorbs or scatters X-rays, and for which further interrogation may be desirable. If the percent transmission is below this predetermined threshold, the second electron beam is directed to the second target, so as to generate a neutron beam (step 2130). The neutron beam then irradiates the object (step 2060), as in FIG. 1.

The emission of gamma rays and/or fission neutrons from the object may be measured (step 2140), for example using gamma ray/fission neutron detector 1090. If, based on the measured emission, the object still appears suspicious, then the object may be further interrogated with the neutron beam, represented by arrow 2160. If, based on the measured emission, the object instead is no longer deemed suspicious, then method 2000 of FIG. 2A may be performed on a different portion of the same object than previously interrogated, or on a new object (step 2150). Optionally, if the object is still deemed suspicious, then the portion of the object may be flagged for manual inspection, and method 2000 allowed to proceed on a different portion of the same object or on a new object (step 2150).

Figure 3B:
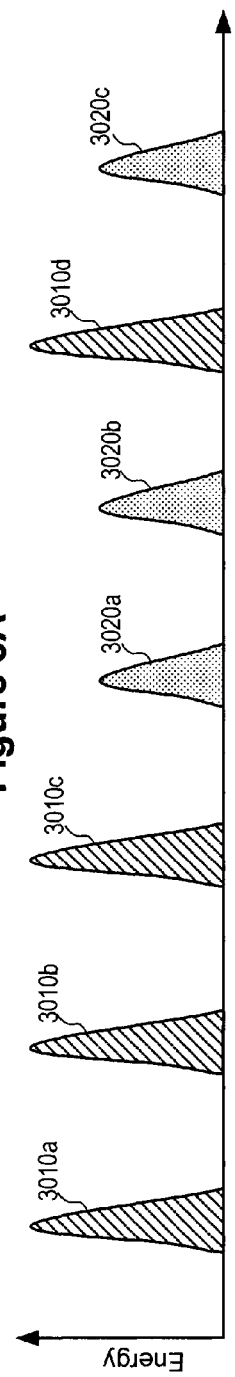

FIG. 3B illustrates an exemplary sequence of pulses that may be generated while performing methods 2000 and 2100. First, X-ray pulses 3010*a*, 3010*b*, and 3010*c* are generated by scanning different portions of object 1070. In this example, the percent transmission of X-ray pulses 3010*a* and 3010*b* is above the predetermined threshold, so the portions of the object interrogated by those pulses are not deemed "suspicious." However, the percent transmission of X-ray pulse 3010*c* is below the predetermined threshold, so the portion of the object interrogated by that pulse is deemed "suspicious" and the second electron beam is directed to the second target so as to generate neutron pulse 3020*a*, with which that portion of the object is irradiated (steps 2130 and 2060 of FIG. 2B). Based on the measurement of gamma ray/fission neutron emission from the object, the object is still deemed suspicious, and therefore is irradiated again with neutron pulse 3020*b* (steps 2140 and 2160 of FIG. 2B). Following such irradiation, the portion of object may be deemed no longer deemed suspicious, or may be flagged for later manual inspection so that the automated scanning may proceed on the remainder of the object. Then, another portion of the object is interrogated with X-ray pulse 3010*d* and deemed suspicious, and so is interrogated with neutron pulse 3020*c*. Note that the above-described sequence is purely illustrative of one possible sequence of pulses that may be generated while performing methods 2000 and 2100.

In some embodiments, system 1000 of FIG. 1 is configured to generate multi-energy X-rays as well as neutrons. For example, method 2200 illustrated in FIG. 2C includes generating first, second, and third electron beams respectively having first, second, and third energies with a single linear accelerator, at first, second and third times (step 2210). Optionally, each such electron beam may have a selected dose based on beam current and/or pulse width, such as described above with reference to step 2020 of FIG. 2A.

The first electron beam may be directed to the first target to generate a first X-ray beam having a first X-ray energy (step 2220), and the object irradiated with the first X-ray beam (step 2230). The second electron beam also may be directed to the first target to generate a second X-ray beam having a second X-ray energy (step 2240), and the object irradiated with the second X-ray beam (step 2250). The second X-ray energy may be greater than, or less than, the first X-ray energy. For example, the first X-ray energy may be 2 MeV, 4 MeV, 6 MeV, or 9 MeV, and the second X-ray energy may be any other of these energies.

Figure 3C:
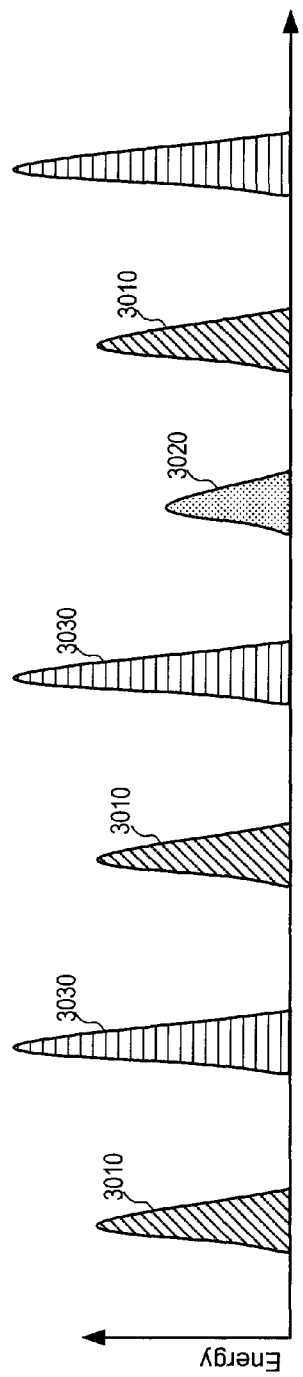

The third electron beam may be directed to the second target to generate a neutron beam (step 2260), and the object irradiated with the neutron beam (step 2270). The first and second X-ray beams and the neutron beam may be interleaved with one another on a pulse-by-pulse basis, analogously as illustrated in FIG. 2A. Method 2200 also is fully compatible with method 2100. Specifically, the first and second X-ray beams may be interleaved with one another with a predetermined frequency, and neutrons generated only when a material is deemed "suspicious" based on the percent transmission of the first and/or second X-ray beams through the object. For example, as illustrated in FIG. 3C, first X-ray pulses 3010 are interleaved on a pulse-by-pulse basis with second X-ray pulses 3030. After an arbitrary number of such interleaving sequences, two in the illustrated embodiment, a portion of the object is deemed "suspicious" and neutron pulse 3020 is generated. Based on the measurement of neutrons emitted by the object based on neutron pulse 3020, the object is no longer deemed suspicious and interleaving of first X-ray pulses 3010 and second X-ray pulses 3030 continues. As such, neutrons may be generated on an aperiodic basis, that is, at arbitrary times relative to X-ray generation and responsive to signals indicating a need for enhanced interrogation of a particular object, or a particular region of an object. Indeed, hundreds, or even thousands of X-ray pulses may be generated for each neutron pulse.

A TW linear accelerator that is particularly well suited for use in the systems and methods of the present invention will now be described. For further detail on this TW linear accelerator, see commonly owned U.S. Patent Publication No. 2010/0188027, entitled "Traveling Wave Linear Accelerator Comprising a Frequency Controller for Interleaved Multi-Energy Operation," the entire contents of which are incorporated by reference herein. An alternative TW linear accelerator that may be used in the systems and methods of the present invention is described in commonly owned U.S. Patent Publication No. 2011/0188638, entitled "Magnetron Powered Linear Accelerator For Interleaved Multi-Energy Operation," the entire contents of which are incorporated by reference herein. Note that although TW linear accelerators may be preferred, SW linear accelerators capable of interleaved multi-energy operation also may be suitable for use in the systems and methods of the present invention. For further details on such SW linear accelerators, see commonly owned U.S. Patent Publication No. 2011/0216886, entitled "Interleaving Multi-Energy X-ray Energy Operation of a Standing Wave Linear Accelerator," U.S. Patent Publication No. 2011/0006708, entitled "Interleaving Multi-Energy X-ray Energy Operation of a Standing Wave Linear Accelerator Using Electronic Switches," the entire contents of which are incorporated by reference herein.

Figure 4:
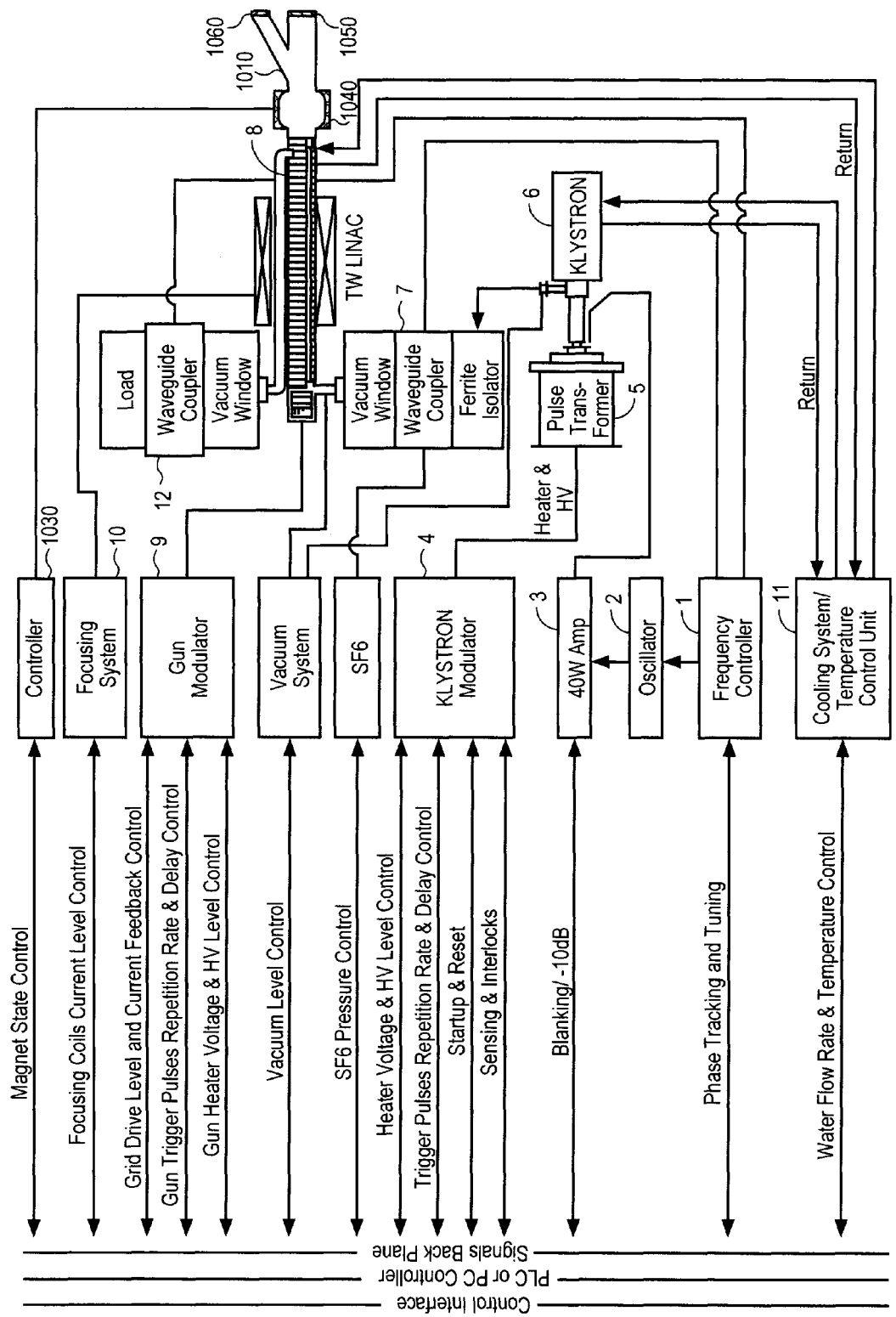
FIG. 4 illustrates a block diagram of a multi-energy traveling wave linear accelerator coupled to the system of FIG. 1.

FIG. 4 illustrates a block diagram of an exemplary multi-energy traveling wave linear accelerator suitable for use with various embodiments of the present invention. The illustrated traveling wave linear accelerator (TW LINAC) includes a control interface through which a user can adjust settings, control operation, etc. of the TW LINAC, as well as of magnet 1040 described further above. The control interface communicates with a programmable logic controller (PLC) and/or a personal computer (PC) that is connected to a signal backplane. The signal backplane provides control signals to multiple different components of the TW LINAC based on instructions received from the PLC, PC and/or control interface.

A frequency controller 1 receives phase tracking and tuning control information from the signal backplane. The frequency controller 1 can be configured to operate at a single frequency setting or to alternate between two or more different frequency settings. For example, the frequency controller 1 can be configured to alternate between a frequency of 9290 Hz and a frequency of 9291 Hz, 400 times per second. Alternatively, the frequency controller 1 may be configured to alternate between more than two different frequencies. In an example, based on the comparison of the measured phase shift of the frequency through the TW LINAC on the previous pulse of the same energy with the set point for energy of the next pulse, the frequency controller 1 adjusts settings of an oscillator 2. By modifying the frequency of the RF signal generated by the oscillator 2, the frequency controller 1 can change the frequency of electromagnetic waves (carrier waves) produced by a klystron 6 on a pulse by pulse basis. Frequency shifts on the order of one or a few parts in 10,000 can be achieved.

The frequency controller 1 may be a phase detection frequency controller, and can use phase vs. frequency response to establish a correct frequency setting. The frequency controller 1, by monitoring and correcting the phase shift from the input to the output of the accelerator, can correct for medium and slow drifts in either the RF frequency or the temperature of the accelerator structure 8. The frequency controller 1 can operate as an automatic frequency control (AFC) system. In an example, the frequency controller 1 can be a multi-frequency controller, and can operate at a set point for each of several different frequencies, with each frequency being associated with each different energy. The frequency controller, including the AFC, is discussed further below.

The oscillator 2 generates an RF signal having a frequency that is provided by the frequency controller 1. The oscillator 2 is a stable low level tunable RF source that can shift in frequency rapidly (e.g., between pulses generated by the klystron modulator 4). The oscillator 2 can generate an RF signal at the milliwatt level. The RF signal is amplified by an amplifier 3 (e.g., a 40 Watt amplifier), and supplied to a klystron 6. The amplifier 3 can be a solid state amplifier or a traveling wave tube (TWT) amplifier, and can amplify the received RF signal to a level required for input to the klystron 6. In an example, the amplifier 3 can be configured to change the output power level, on a pulse to pulse basis, to the level appropriate for the energy of an upcoming LINAC pulse. Alternatively, the klystron modulator 4 could deliver different high voltage pulses to the klystron 6 for each beam energy required.

A klystron modulator 4 receives heater and high voltage (HV) level control, trigger pulse and delay control, startup and reset, and sensing and interlock signals from the signal backplane. The klystron modulator 4 is a capable of generating high peak power pulses to a pulse transformer. The effective output power of the klystron modulator 4 is the power of the flat-top portion of the high voltage output pulse. The klystron modulator 4 can be configured to generate a new pulse at each frequency change in the frequency controller 1. For example, a first pulse may be generated when the frequency controller 1 causes the oscillator 2 to generate an RF signal having a first frequency, a second pulse may be generated when the frequency controller 1 causes the oscillator 2 to generate an RF signal having a second frequency, a third pulse may be generated when the frequency controller 1 causes the oscillator 2 to generate an RF signal having the first frequency, and so on.

The klystron modulator 4 drives energy into a pulse transformer 5 in the form of repeated high energy approximately square wave pulses. The pulse transformer 5 increases the received pulses into higher energy voltage pulses with a medium to high step-up ratio. The transformed pulses are applied to the klystron 6 for the generation of high energy microwave pulses. The rise time of the output pulse of the klystron modulator 4 is dominated by the rise time of the pulse transformer 5, and therefore the pulse transformer 5 is configured to have a fast rise time to approximate square waves.

The klystron 6 is a linear-beam vacuum tube that generates high power electromagnetic waves (carrier waves) based on the received modulator pulses and the received oscillator radio frequency (RF) signal. The klystron 6 provides the driving force that powers the linear accelerator. The klystron 6 coherently amplifies the input RF signal to output high power electromagnetic waves that have precisely controlled amplitude, frequency and input to output phase in the TW LINAC accelerator structure. The klystron 6 operates under pulsed conditions, which enables the klystron 6 to function using a smaller power source and require less cooling as compared to a continuous power device. The klystron 6 typically has a band width on the order of one percent or more.

The klystron 6 is an amplifier, therefore, the output RF signal generated by the klystron 6 has the same frequency as the low power RF signal input to the klystron 6. Thus, changing the frequency of the high power RF electromagnetic wave used to drive the LINAC can be achieved simply by changing the frequency of the low power RF signal used to drive the klystron 6. This can be easily performed between pulses with low power solid state electronics. Similarly, the output power of the electromagnetic wave from the klystron can be changed from pulse to pulse by just changing the power out of the amplifier 3.

A waveguide 7 couples the klystron 6 to an input of an accelerator structure 8 of the TW LINAC. The waveguide 7 includes a waveguide coupler and a vacuum window. The waveguide 7 carries high powered electromagnetic waves (carrier waves) generated by the klystron 6 to the accelerator structure 8. The waveguide coupler of waveguide 7 can sample a portion of the electromagnetic wave power to the input of the LINAC. A waveguide 12 that includes a waveguide coupler and a vacuum window couples the output of the accelerator structure 8 to the RF load. The waveguide coupler of waveguide 12 can sample a portion of the electromagnetic wave power to the output of the LINAC. A phase comparator of frequency controller 1 can be used to compare a signal from the waveguide coupler of waveguide 7 to a signal from the waveguide coupler of waveguide 12 to determine the phase shift of the electromagnetic wave through accelerator structure 8. The frequency controller 1 uses the phase shift of the electromagnetic wave to determine the frequency correction to be applied at the klystron, if any. Waveguide 7 or waveguide 12 can be a rectangular or circular metallic pipe that is configured to optimally guide waves in the frequencies that are used to accelerate electrons within the LINAC without significant loss in intensity. The metallic pipe can be a low-Z, high conductivity, material such as copper. To provide the highest field gradient possible with near maximum input power, the waveguide coupler can be filled with $SF_6$ gas. Alternatively, the waveguide can be evacuated.

The vacuum window permits the high power electromagnetic waves to enter the accelerator structure 8 while separating the evacuated interior of the accelerator structure 8 from its gas filled or evacuated exterior.

A gun modulator 9 controls an electron gun (not shown) that fires electrons into the accelerator structure 8. The gun modulator 9 receives grid drive level and current feedback control signal information from the signal backplane. The gun modulator 9 further receives gun trigger pulses and delay control pulse and gun heater voltage and HV level control from the signal backplane. The gun modulator 9 controls the electron gun by instructing it when and how to fire (e.g., including repetition rate and grid drive level to use). The gun modulator 9 can cause the electron gun to fire the electrons at a pulse repetition rate that corresponds to the pulse repetition rate of the high power electromagnetic waves (carrier waves) supplied by the klystron 6.

An example electron gun includes an anode, a grid, a cathode and a filament. The filament is heated to cause the cathode to release electrons, which are accelerated away from the cathode and towards the anode at high speed. The anode can focus the stream of emitted electrons into a beam of a controlled diameter. The grid can be positioned between the anode and the cathode.

The electron gun is followed by a buncher that is located after the electron gun and is typically integral with the accelerating structure. In one embodiment, the buncher is composed of the first few cells of the accelerating structure. The buncher packs the electrons fired by the electron gun into bunches and produces an initial acceleration. Bunching is achieved because the electrons receive more energy from the electromagnetic wave (more acceleration) depending on how near they are to the crest of the electromagnetic wave. Therefore, electrons riding higher on the electromagnetic wave catch up to slower electrons that are riding lower on the electromagnetic wave. The buncher applies the high power electromagnetic waves provided by the klystron 6 to the electron bunch to achieve electron bunching and the initial acceleration.

High power electromagnetic waves are injected into the accelerator structure 8 from the klystron 6 via the waveguide 7. Electrons to be accelerated are injected into the accelerator structure 8 by the electron gun. The electrons enter the accelerator structure 8 and are typically bunched in the first few cells of the accelerator structure 8 (which may comprise the buncher). The accelerator structure 8 is a vacuum tube that includes a sequence of tuned cavities separated by irises. The tuned cavities of the accelerator structure 8 are bounded by conducting materials such as copper to keep the RF energy of the high power electromagnetic waves from radiating away from the accelerator structure 8.

The tuned cavities are configured to manage the distribution of electromagnetic fields within the accelerator structure 8 and distribution of the electrons within the electron beam. The high power electromagnetic waves travel at approximately the same speed as the bunched electrons so that the electrons experience an accelerating electric field continuously. In the first portion of the TW LINAC, each successive cavity is longer than its predecessor to account for the increasing particle speed. Typically, after the first dozen or so cells the electrons reach about 98% of the velocity of light and the rest of the cells are all the same length. The basic design criterion is that the phase velocity of the electromagnetic waves matches the particle velocity at the locations of the accelerator structure 8 where acceleration occurs.

Once the electron beam has been accelerated by the accelerator structure 8, it is directed toward target structure 1010, which includes first and second targets 1050, 1060 and magnet 1040 such as illustrated in FIG. 1 and may be configured as described further below with reference to FIG. 5. The bombardment of the first target 1050 by the first electron beam generates a beam of X-rays (discussed further below), while the bombardment of the second target 1060 with the second electron beam generates a beam of neutrons. The electrons can be accelerated to different energies before they strike their respective targets. In an interleaving operation, the electrons can be alternately accelerated to two or more different output energies, e.g., to 6 mega electron volts (MeV)[1] and to 9 MeV. Alternately, the electrons can be accelerated to different energies. Magnet 1040 may be coupled to controller 1030 as described further above with reference to FIG. 1, and controller 1030 may be coupled to the control interface of the TW LINAC via the PLC or PC controller and signals back plane.

One electron volt equals $1.602 \times 10^{-19}$ joule. Therefore, 6 MeV=$9.612 \times 10^{-13}$ joule.

To achieve a light weight and compact size, the TW LINAC may operate in the X-band (e.g., at an RF frequency between 8 GHz and 12.4 GHz). The high operating frequency, relative to a conventional S-band LINAC, reduces the length of the accelerator structure 8 by approximately a factor of three, for a given number of accelerating cavities, with a concomitant reduction in mass and weight. As a result, all of the essential components of the TW LINAC may be packaged in a relatively compact assembly. Alternatively, the TW LINAC may operate in the S-band. Such a TW LINAC requires a larger assembly, but can provide a higher energy X-ray beam (e.g., up to about 18 MeV) with commercially available high power electromagnetic wave sources.

A focusing system 10 controls powerful electromagnets that surround the accelerator structure 8. The focusing system 10 receives a current level control from the signal backplane, and controls a current level of focusing coils to focus an electron beam that travels through the accelerator structure 8. The focusing system 10 is designed to focus the beam to concentrate the electrons to a specified diameter beam that is able to strike a small area of the target. The beam can be focused and aligned by controlling the current that is supplied to the electromagnet. In an example, the focusing current is not changed between pulses, and the current is maintained at a value which allows the electromagnet to substantially focus the beam for each of the different energies of operation.

A sulfur hexafluoride ($SF_6$) controller controls an amount (e.g., at a specified pressure) of $SF_6$ gas that can be pumped into the waveguide. The $SF_6$ controller receives pressure control information from the backplane and uses the received information to control the pressure of $SF_6$ gas that is supplied to the waveguide. $SF_6$ gas is a strong electronegative molecule, giving it an affinity for free electrons. Therefore, the $SF_6$ gas is used as a dielectric gas and insulating material, and can be provided to waveguide 7 and waveguide 12 to quench arcs that might otherwise occur. The $SF_6$ gas increases the amount of peak power that can be transmitted through the waveguide 7, and can increase the voltage rating of the TW LINAC.

A vacuum system (e.g., an ion pump vacuum system) can be used to maintain a vacuum in both the klystron 6 and the accelerator structure 8. A vacuum system also can be used to generate a vacuum in portions of the waveguide 7. In air, intense electric and magnetic fields cause arcing, which destroys the microwaves, and which can damage the klystron, waveguide or accelerator structure. Additionally, within the accelerator structure 8, any beams that collide with air molecules are knocked out of the beam bunch and lost. Evacuating the chambers prevents or minimizes such occurrences.

The vacuum system may report current vacuum levels (pressure) to the signal backplane. If pressure of the klystron 6 or accelerator structure 8 exceed a pressure threshold, the vacuum system may transmit a command to the signal backplane to turn off the klystron 6 until an acceptable vacuum level is reached.

Many components of the TW LINAC can generate heat. Heat can be generated, for example, due to the electromagnetic wave power loss on the inner walls of the accelerator, by the electron bombardment of the target at the end of the accelerator structure 8, and by the klystron 6. Since an increase in temperature causes metal to expand, temperature changes affect the size and shape of cavities within the accelerator structure, the klystron, the waveguide, etc. This can cause the frequency at which the wave is synchronous with the beam to change with the temperature. The proper operation of the accelerator requires careful maintenance of the cavity synchronous frequency to the passage of beam bunches. Therefore, a cooling system 11 is used to maintain a constant temperature and minimize shifts in the synchronous frequency.

The cooling system 11 circulates water or other coolant to regions that need to be cooled, such as the klystron 6 and the accelerator structure 8. Through the signal backplane, the cooling system 11 receives water flow rate and temperature control information. The cooling system 11 can be used to monitor the temperature of the klystron 6 and the accelerator structure 8, and can be configured to maintain a constant temperature in these components. However, the temperature of the metal of the accelerator structure and the klystron may rise as much as 10 degrees when the LINAC is operated at a high repetition rate, which can contribute to the drift in the electromagnetic wave. The frequency controller can be used to compensate for the effect of the drift.

Figure 5:
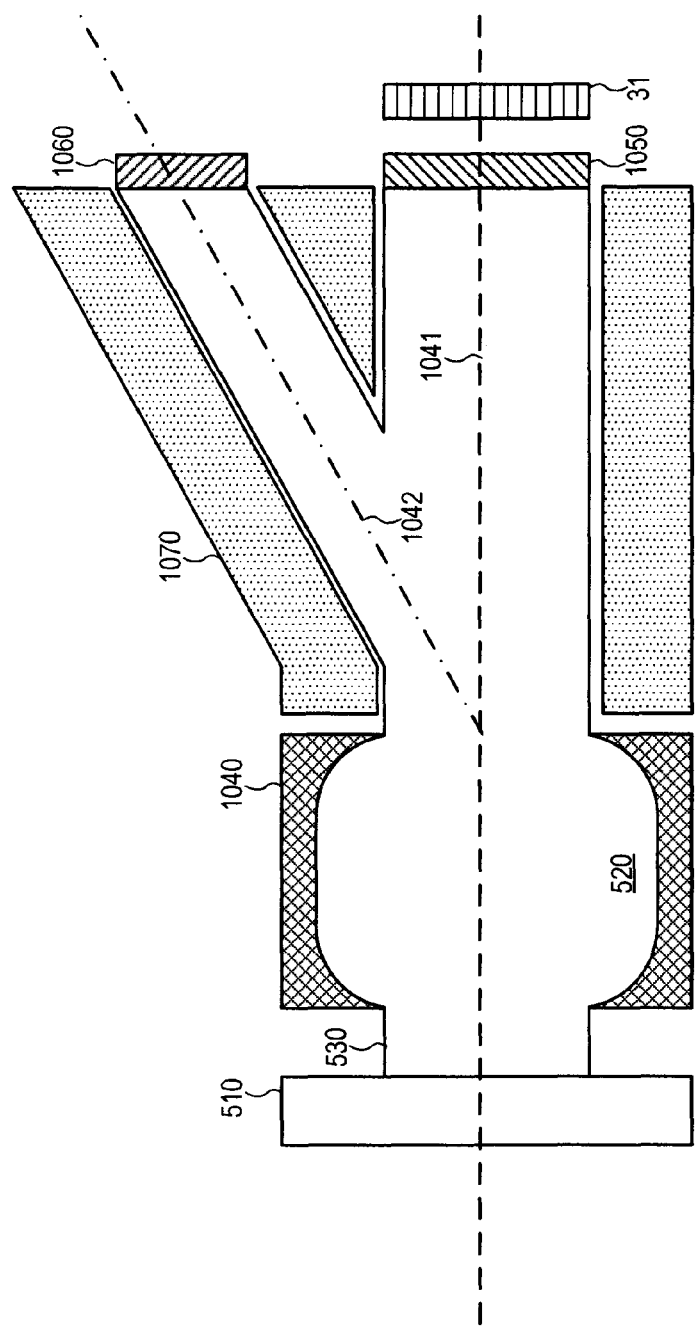
FIG. 5 illustrates a cross-section of a target structure coupled to an accelerator structure that includes targets for generating X-rays and neutrons and a magnet for selectably deflecting an electron beam from the accelerator structure towards one of the targets.

FIG. 5 illustrates a cross-section of target structure 1010 which may be coupled to the accelerator structure 8 (not shown) via flange 510. The target structure 1010 includes first target 1050 to perform the principal conversion of electron energy to X-rays and second target 1060 to perform the principal conversion of electron energy to neutrons. Magnet 1040 is disposed about or adjacent to magnet cavity 520, and is configured to direct electrons received from accelerator structure 8 that pass through magnet cavity 520 either onto beam path A (1041) so as to irradiate first target 1050, or onto beam path B (1042) so as to irradiate second target 1060, responsive to appropriate signals from controller 1030. As noted above, directing electrons onto beam path A need not necessarily require deflection of the electrons. Magnet cavity 520 and first and second targets 1050, 1060 may all be coupled to a common vacuum envelope 530, and may share a common vacuum with accelerator structure 8. Shielding 1070 may surround vacuum envelope 530 so as to help protect the operator and others from radiation.

The first target 1050 may be, for example, an alloy of tungsten and rhenium, where the tungsten is the principle source of X-rays and the rhenium provides thermal and electrical conductivity. In general, the target 1050 may include one or more target materials having an atomic number approximately greater than or equal to 70 to provide efficient X-ray generation. In an example, the X-ray target 1050 can include a low-Z material such as but not limited to copper, which can avoid or minimize generation of neutrons when bombarded by the output electrons. When electrons from the electron beam enter the target 1050, they give up energy in the form of heat and X-rays (photons), and lose velocity. In operation, an accelerated electron beam impinges on the target, generating Bremsstrahlung and k-shell X-rays (see below).

The second target 1060 may be, for example, beryllium, tantalum, depleted uranium, tungsten, or lead. Optionally, second target 1060 may include a stack of two or more separate targets in series with one another, where each target may be formed of a material that is the same as, or different than, other targets in the stack. Such a configuration may provide enhanced selectivity in producing certain types or energies of neutrons and/or enhanced neutron flux. In general, the target 1060 may include one or more target materials having an atomic number selected so as to provide efficient neutron generation.

Each of targets 1050, 1060 may be mounted in a metallic holder (not shown), which may be a good thermal and electrical conductor, such as copper. As is known in the art, each holder may include an electron collector (also not shown) to collect electrons that are not stopped within the targets 1050, 1060 and/or that are generated within the targets 1050, 1060. The collector may be a block of electron absorbing material such as a conductive graphite based compound. In general, the collector may be made of one or more materials with an atomic number approximately less than or equal to 6 to provide both electron absorption and transparency to X-rays or neutrons generated by the targets 1050, 1060. The collector may be electrically isolated from a holder by an insulating layer (e.g., a layer of anodized aluminum). In an example, the collector is a heavily anodized aluminum slug.

A collimator (also not shown) can be attached to the exit side of target structure 1010 so as to shape the X-ray beam (1051) and/or neutron beam (1061) into an appropriate shape. For example, if the TW LINAC is being used as an X-ray source for a cargo inspection system, the collimator may form the X-ray beam generated at target 1050 into a fan shape. The X-ray beam may then penetrate a target (e.g., a cargo container), and a detector at an opposite end of the target may receive X-rays that have not been absorbed or scattered. The received X-rays may be used to determine properties of the target (e.g., contents of a cargo container), and neutrons subsequently generated as appropriate. Preferably, X-ray target 1050 is positioned along a straight portion of beam path 1041, such that the electron beam impinging that target is small and round, thereby facilitating generation of an X-ray beam of similar shape and size and thus facilitating higher quality imaging. By comparison, the positioning of neutron target 1060 may be less sensitive to the shape and size of the electron beam, because the neutron beam may generally flood the imaging area and does not require a pin point reference as an X-ray image may.

An X-ray intensity monitor 31 can be used to monitor the yield of the X-rays during operation (see FIG. 5). A non-limiting example of an X-ray intensity monitor 31 is an ion chamber. The X-ray intensity monitor can be positioned at or near the X-ray source, for example, facing the target. In one embodiment, based on measurements from the X-ray intensity monitor 31 from one pulse of the LINAC to another, the frequency controller can transmit a signal to the one or more oscillators to cause the electromagnetic wave source to generate an electromagnetic wave at a frequency and amplitude to maximize the yield of X-ray at an energy.

The frequency controller 1 can be interfaced with the X-ray intensity monitor 31. The frequency controller 1 can be used to monitor the measurements from the X-ray intensity monitor (which provide an indication of the X-ray yield) and use that information to provide a signal to the oscillator. The oscillator can tune the electromagnetic wave source to generate an electromagnetic wave at a frequency based on the signal from the frequency controller. In an embodiment, the frequency controller be configured to compare a measurement from the X-ray intensity monitor that indicates the yield of the first beam of X-rays emitted in a desired range of X-ray energies to a measurement from the X-ray intensity monitor that indicates the yield of the second beam of X-rays at that range of X-ray energies. The second beam of X-rays can be generated using a set of electrons that is accelerated in the accelerator structure by an electromagnetic wave that has about the same amplitude as that used in the generation of the first beam of X-rays. For example, the electromagnetic waves can have about the same magnitude if they differ by less than about 0.1%, less than about 1%, less that about 2%, less than about 5% in magnitude, less than about 10% in magnitude, or more. The frequency of the electromagnetic wave delivered to the LINAC for generating the second beam of X-rays can differ in magnitude from the frequency of the electromagnetic wave delivered to the LINAC for generating the first beam of X-rays by a small amount ($\delta f$). For example, $\delta f$ be a difference on the order of about one or a few parts in 10,000 of a frequency in kHz. In some embodiments, $\delta f$ can be a difference on the order of about 0.000001 MHz or more, about 0.00001 MHz or more, about 0.001 MHz or more, about 0.01 MHz or more, about 0.03 MHz or more, about 0.05 MHz or more, about 0.08 MHz or more, about 0.1 MHz or more, or about 0.15 MHz or more. The frequency controller can transmit a signal to the oscillator so that the oscillator causes the electromagnetic wave source to generate a subsequent electromagnetic wave at a frequency to maximize the yield of a X-rays in a subsequent operation of the LINAC.

The frequency controller can tune the frequency of the electromagnetic wave by monitoring both (i) the phase shift of the electromagnetic wave from the input to the output of the accelerator structure and (ii) the dose from the X-ray intensity monitor.

In another embodiment, the frequency controller can also be interfaced with an electron energy spectrum monitor (not illustrated). A non-limiting example of an electron energy spectrum monitor is an electron current monitor. For example, an electron current monitor can be configured to measure the current reaching the electron current collector in the target assembly, as will be familiar to those skilled in the art. The electron energy spectrum monitor can be positioned near the output of the accelerator structure. The electron energy spectrum monitor can be used to monitor the electron current of the output of electrons for a given pulse of the LINAC. Based on the measurements from the electron energy spectrum monitor, the frequency controller transmits a signal to the oscillator so that the oscillator tunes the electromagnetic wave source to the desired frequency. In this embodiment, the frequency controller can be configured to compare an indication of a first energy spectrum of a first output of electrons from the output of the accelerator structure to an indication of a second energy spectrum of a second output of electrons from the output of the accelerator structure, and transmit a signal to the oscillator based on the comparison. For example, the frequency controller can be configured to compare a first electron current of the first output of electrons from one pulse of the LINAC to a second electron current of the second output of electrons from another pulse. The second output of electrons can be generated using an electromagnetic wave that has about the same amplitude as that used to generate the first output of electrons. For example, the electromagnetic waves can have about the same magnitude if they differ by less than about 0.1%, less than about 1%, less that about 2%, less than about 5% in magnitude, less than about 10% in magnitude, or more. The frequency of the electromagnetic wave delivered to the LINAC for generating the second output of electrons can differ in magnitude from the frequency of the electromagnetic wave delivered to the LINAC for generating the first output of electrons by a small amount ($\delta f$). For example, Ube a difference on the order of about one or a few parts in 10,000 of a frequency in kHz. In some embodiments, $\delta f$ can be a difference on the order of about 0.000001 MHz or more, about 0.00001 MHz or more, about 0.001 MHz or more, about 0.01 MHz or more, about 0.03 MHz or more, about 0.05 MHz or more, about 0.08 MHz or more, about 0.1 MHz or more, or about 0.15 MHz or more. Based on the signal from the frequency controller, the oscillator can cause the electromagnetic wave source to generate a subsequent electromagnetic wave at a frequency to stabilize the energy of a subsequent output of electrons.

In an embodiment, the frequency controller can tune the frequency of the electromagnetic wave by monitoring both (i) the phase shift of the electromagnetic wave from the input and the output of the accelerator structure and (ii) the electron current of the output of electrons.

In yet another embodiment, the frequency controller can tune the electromagnetic wave source primarily by monitoring the phase shift of the electromagnetic wave from the input and the output of the accelerator structure, and as a secondary measure can monitor the doses of the X-ray intensity monitor and the electron current of the output of electrons.

The frequency controller can be configured to tune the frequency of the electromagnetic wave source, based on the monitoring of the phase, X-ray yield, and/or energy spectrum of the output electrons from pulses of the LINAC as described herein, in an iterative process. That is, the frequency controller can be configured to tune the electromagnetic wave source in an iterative process so that, with each subsequent pulse of the LINAC for a given energy of operation, the yield of X-rays is further improved until it reaches the maximum or is maintained at the maximum, or the stability of the energy spectrum of the output of electrons is further increased or maintained.

Multi-Energy Traveling Wave Linear Accelerator Operation Theory

In a one energy LINAC, the accelerator structure 8 is configured such that the electron bunch rides at the crest of the high energy electromagnetic waves throughout the accelerator structure 8, except in the first few cells of the accelerator structure 8 that comprise the buncher. This can be accomplished by ensuring that the electric field of the electromagnetic waves remains in phase with the electron bunches that are being accelerated. An electron bunch that rides at the crest of the electromagnetic wave receives more energy than an electron bunch that rides off the crest, which increases efficiency of the LINAC. Moreover, the crest of the electromagnetic wave has a slope of zero. Therefore, if jitter occurs to cause the electron bunch to move off of the crest of the wave, the amount of energy imparted to the electron bunch changes only by a very small amount. For these reasons, it is desirable to have the electron bunch ride the crest of the electromagnetic waves.

Figure 6:
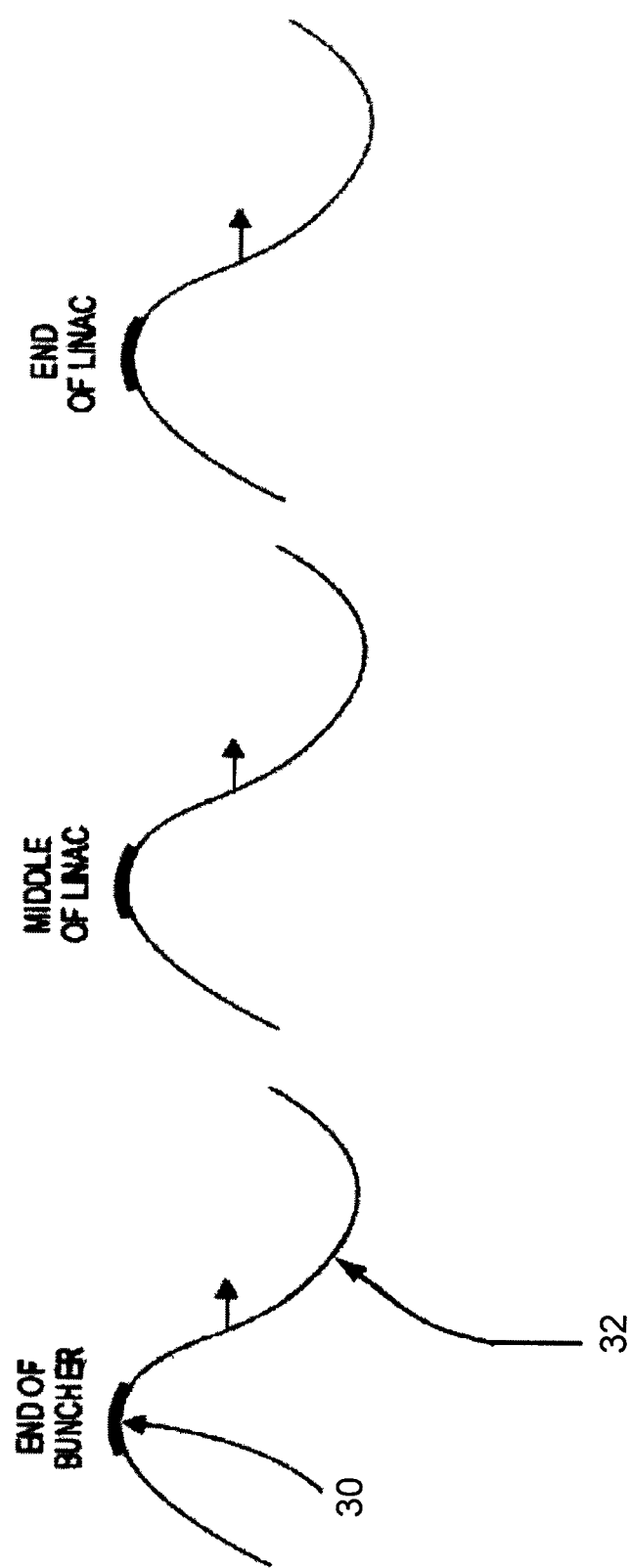
FIG. 6 illustrates an electron bunch riding an electromagnetic wave at three different regions in an accelerator structure.

FIG. 6 illustrates an electron bunch 30 riding an electromagnetic wave 32 (also referred to as a carrier wave) at the beginning of the accelerator structure (just after exiting the buncher), at the middle of the accelerator structure, and at the end of the accelerator structure (just before striking the target). FIG. 6 illustrates a higher energy operation of the LINAC, where electron bunch 30 can ride substantially at the crest of the electromagnetic wave 32 at each region of the accelerator structure (substantially synchronous).

In a multi-energy LINAC, the accelerator structure is typically configured such that at the higher energy operation the electron bunches 30 ride at the crests of the high energy electromagnetic waves 32, as is shown in FIG. 6. However, to impart less energy on the electron beam for the lower energy operation, the strength (amplitude) of the electromagnetic wave can be reduced by reducing the output power of the klystron 6 (e.g., by reducing the input drive power to the klystron 6 or by reducing the klystron high voltage pulse). As another example way to impart less energy on the electron beam for the lower energy operation, the acceleration imparted by the electromagnetic wave also can be reduced by increasing the beam current from the electron gun in an effect referred to as beam loading (described below). The lower strength electromagnetic wave accelerates the electron bunches at a slower rate than the higher strength electromagnetic waves. Therefore, when the RF field amplitude is lowered to lower the energy of the X-ray beam, the electron bunches gain energy less rapidly in the buncher and so end up behind the crest of the wave at the end of the buncher. This causes the electron bunches to fall behind the crest of the waves by the end of the buncher region of the accelerator structure. If the RF frequency is the same for the low energy level as for the high energy level, the bunch will stay behind the crest in the accelerator structure, resulting in a broad, undesirable, energy spectrum.

When the electron bunch does not travel at the crest of the electromagnetic wave, the efficiency of the LINAC is reduced, and therefore greater power is required than would otherwise be necessary to generate the lower power X-ray beam. More importantly, since the electron bunch is not at the crest of the wave, any jitter can cause the electron bunch to move up or down on the electromagnetic sine wave. Thus, the energy of the X-ray beam will fluctuate in response to phase fluctuations caused by jitter in the RF frequency and amplitude and variation in the accelerator structure temperature. This changes the amount of energy that is imparted to the electron bunch, which causes instability and reduces repeatability of the resultant X-ray beam.

Three typical sources of jitter include frequency jitter from the RF source, temperature variation from the accelerator structure and amplitude jitter from the RF source. All three sources of jitter can cause the electron bunch to move up or down on the electromagnetic sine wave. Additionally, amplitude jitter of the RF source also can cause jitter in the amplitude of the accelerating fields throughout the LINAC.

A standing wave LINAC has a fixed number of half wavelengths from one end of the accelerator structure to the other, equal to the number of resonant accelerating cavities. Therefore, the phase velocity of the electromagnetic waves cannot be changed in a standing wave LINAC. For the standing wave LINAC, when the frequency of the electromagnetic wave is changed, the electromagnetic wave moves off the resonance frequency of the accelerator structure, and the amplitude of the electromagnetic waves decreases. However, the phase velocity is still the same, and the accelerator structure still has the same number of half wavelengths. Therefore, the standing wave LINAC cannot be adjusted to cause the electron bunch to ride at the crest of the electromagnetic wave for multiple energy levels.

Traveling wave LINACS have the property that rather than having discrete modes (as in a standing wave LINAC), they have a continuous pass band in which the phase velocity (velocity of the electromagnetic wave) varies continuously with varying frequency. In a TW LINAC the phase velocity of the electromagnetic wave can be changed with the change in frequency.

Figure 7:
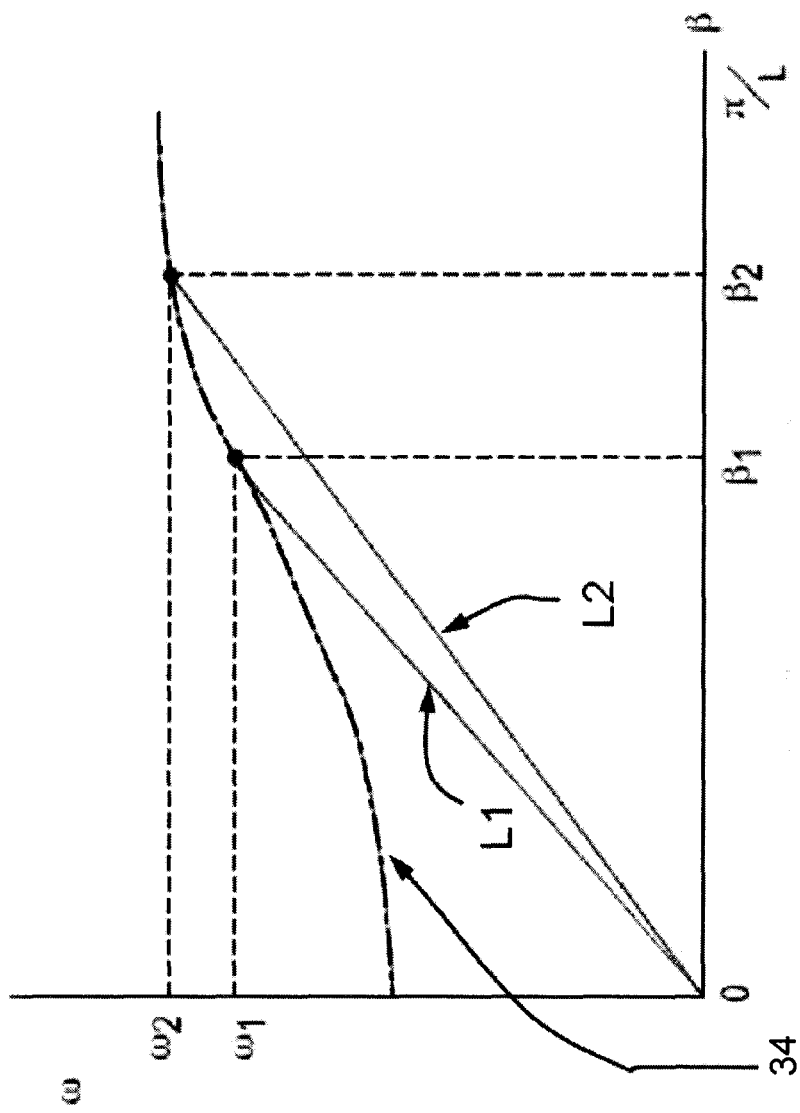
FIG. 7 illustrates a dispersion curve for an exemplary TW LINAC after an electron beam has passed through the buncher.

FIG. 7 illustrates a dispersion curve 34 for an exemplary TW LINAC. The dispersion curve 34 in FIG. 7 graphs angular frequency ($\omega = 2\pi f$, wherein f is the frequency of the electromagnetic wave in the accelerator structure) vs. the propagation constant $\beta \equiv 2\pi/\lambda$, where $\lambda$ is the wavelength of the electromagnetic wave in the accelerator structure) for the exemplary TW LINAC. The propagation constant, $\beta$, is the phase shift of the RF electromagnetic wave per unit distance along the Z axis of the TW LINAC. The phase velocity of an electromagnetic wave in the TW LINAC is equal to the slope, $\omega/\beta$, of the line from the origin to the operating point, $\omega,\beta$, which is equal to the frequency times the wavelength of the electromagnetic wave ($f\lambda$). As shown, the phase velocity of the electromagnetic wave varies continuously with varying frequency. The group velocity (the velocity with which a pulse of the electromagnetic wave propagates) is given by $d\omega/d\beta$, the slope of the dispersion curve. The change of phase, $\delta\phi(z)$, at a longitudinal position z in the TW LINAC caused by a change of angular frequency $\delta\omega$, is given by the equation:

$$\delta\phi(z) = \delta\omega \int dz/(d\omega/d\beta) = \delta\omega \int dz/v_g = \delta\omega t_f(z) \quad (1)$$

where $t_f(z)$ is the filling time from the beginning of the LINAC to the position z.

It is important to realize that in general for LINACs the dispersion curve, and therefore both the phase velocity and the group velocity, can vary from cell to cell. In the TW LINAC used as an example here, for the maximum energy operation most of the LINAC has a constant phase velocity equal to the velocity of light. However, the structure is designed to have an approximately constant gradient, which means that the group velocity decreases approximately linearly with distance along the LINAC. Therefore, when the frequency is changed (raised) for operation at the lower energy level (e.g., at 6 MeV), to achieve a maximum possible energy the phase velocity is no longer constant during the portion of acceleration at which the electrons travel at approximately the speed of light.

As the angular frequency of an electromagnetic wave is increased in the TW LINAC, the phase velocity of the electromagnetic wave is decreased. Thus, if the angular frequency of an electromagnetic wave used to generate a high energy electron beam is $\omega_1$ and the angular frequency of an electromagnetic wave used to generate a low energy electron beam is $\omega_2$, the slope of $\omega_1/\beta_1$ (L1) will be steeper than the slope of $\omega_2/\beta_2$ (L2). Accordingly, the phase velocity of the electromagnetic wave that generates the high energy X-ray beam is higher than the phase velocity of the electromagnetic wave that generates the low energy X-ray beam. The angular frequency of the electromagnetic wave used to generate the high energy X-ray beam can be chosen such that the phase velocity for the electromagnetic wave ($\omega_1/\beta_1$) is approximately equal to the speed of light, through most of the LINAC.

Figure 8:
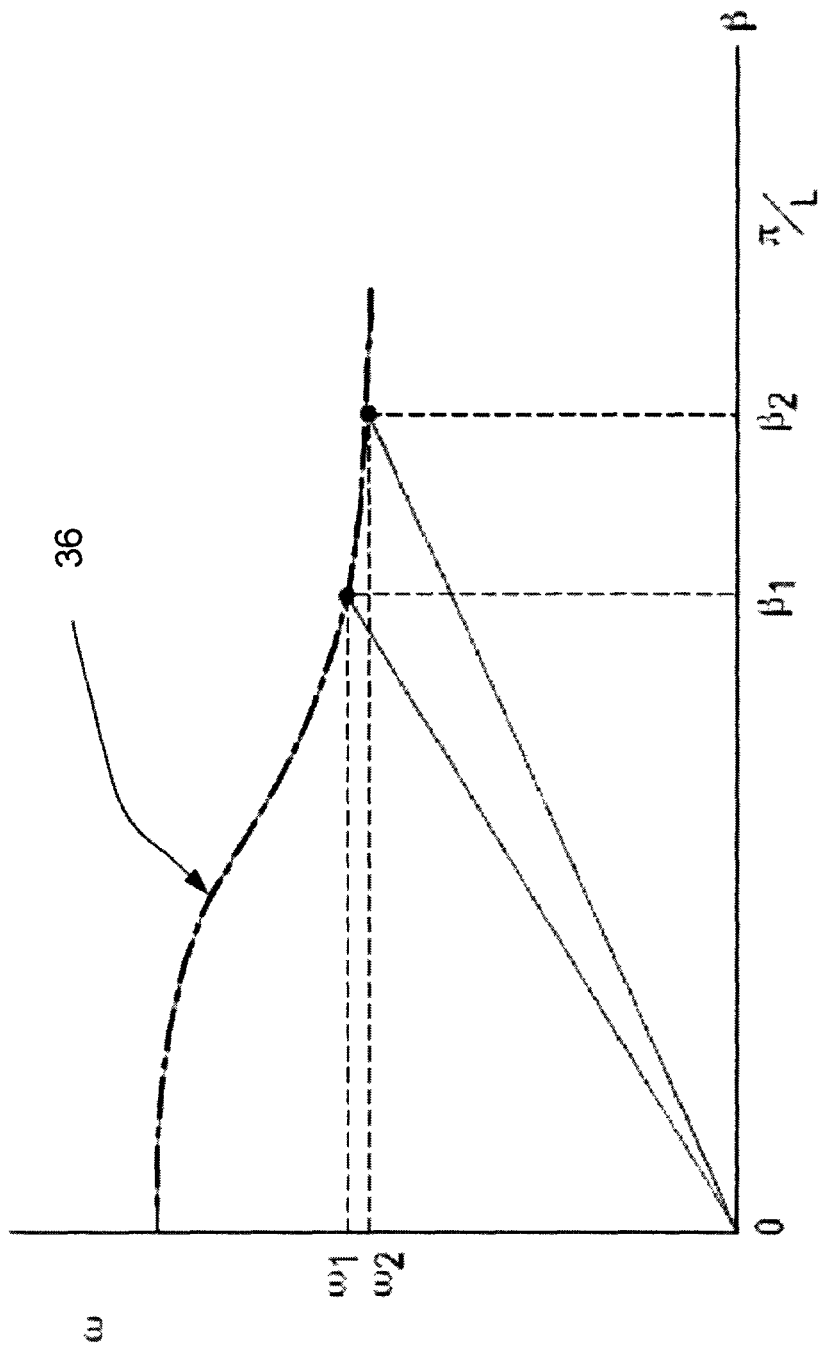
FIG. 8 illustrates a dispersion curve for a high efficiency magnetically coupled reentrant cavity traveling wave LINAC.

FIG. 8 illustrates a dispersion curve 36 for a high efficiency magnetically coupled reentrant cavity traveling wave LINAC. In the dispersion curve 36 in FIG. 8, the y-axis represents angular frequency and the X-axis represents propagation constants. As shown, in the high efficiency magnetically coupled reentry cavity TW LINAC configuration, the phase velocity varies continuously with changing frequency. However, the dispersion curve 36 of FIG. 8 shows a different relationship between angular frequency and phase velocity than is shown in the dispersion curve 34 of FIG. 7. For example, in the dispersion curve 36 of FIG. 8, angular frequency associated with the high energy electron beam is higher than the angular frequency associated with the low energy electron beam. This is in contrast to the dispersion curve 34 of FIG. 7, in which the angular frequency associated with the high energy beam is lower than the angular frequency associated with the low energy electron beam. The relationship between angular frequency and phase velocity can differ from LINAC to LINAC, and therefore the specific angular frequencies that are used to tune a TW LINAC should be chosen based on the relationship between angular frequency and phase velocity for the TW LINAC that is being tuned. A magnetically coupled backward wave traveling wave constant gradient LINAC with nose cones operating near the $3\pi/4$ or $4\pi/5$ mode could have a shunt impedance and therefore efficiency as high as a cavity coupled standing wave accelerator.

In one embodiment, the phase velocity of the electromagnetic wave can be adjusted to cause the electron bunch to, on average, travel at the crest of the electromagnetic wave. Alternately, the phase velocity of the electromagnetic wave can be adjusted to cause the electron bunch to, on average, travel ahead of the crest of the electromagnetic wave. Adjustments to the phase velocity can be achieved for multiple different energy levels simply by changing the frequency of the electromagnetic wave to an appropriate level. Such an appropriate level can be determined based on the dispersion curves as shown in FIGS. 7 and 8. For example, the RF frequency of the electromagnetic wave can be raised to reduce the phase velocity of the wave so that the electron bunch moves faster than the wave and drifts up toward the crest as it travels through the accelerator. Changing the RF frequency of the TW LINAC is easy to do on a pulse to pulse basis if the RF source is a klystron 6, thus allowing interleaving of 2 or more energies at a high repetition rate. Frequency changes can also be made when other RF sources are used. This strategy will work for a wide energy range (e.g., including either the full single structure X-band or the full single structure S-band energy range).

Figure 9:
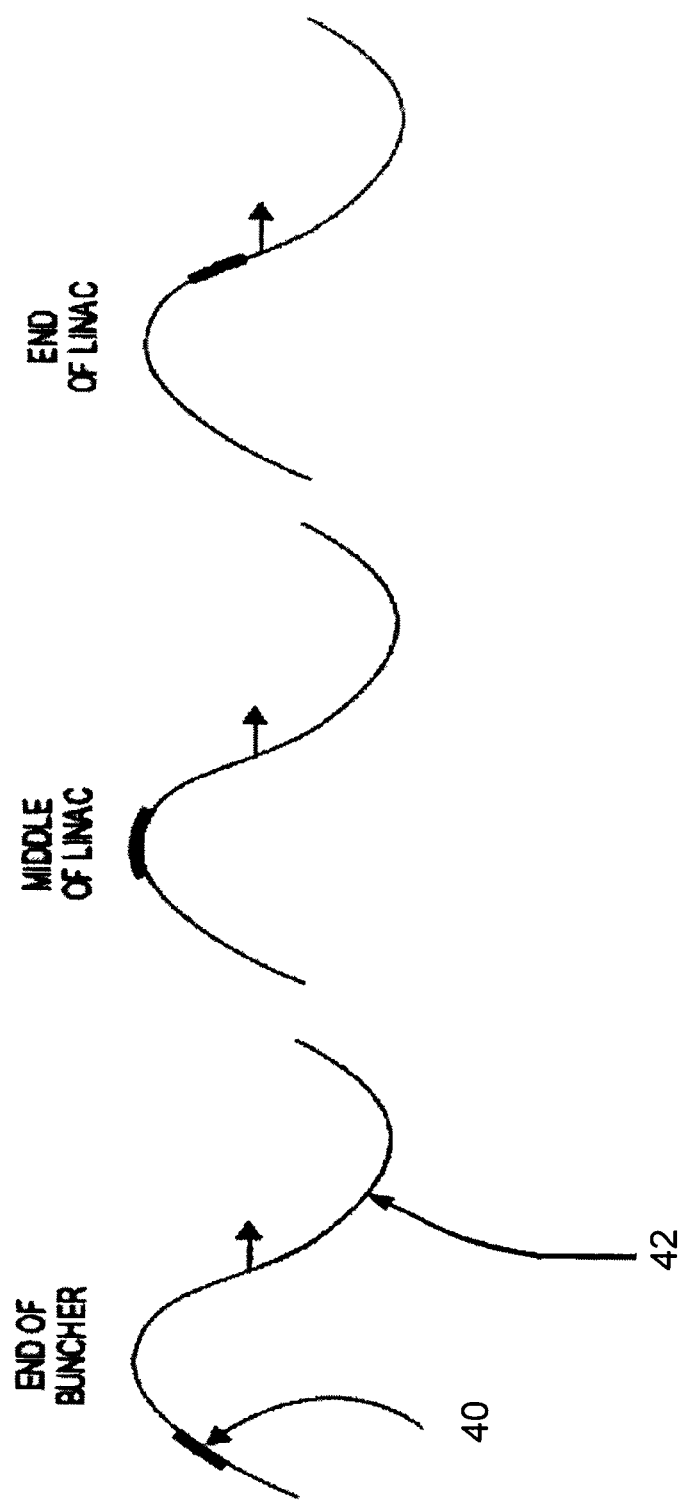
FIG. 9 illustrates an electron bunch riding an electromagnetic wave at three different regions in an accelerator structure of a TW LINAC.

FIG. 9 illustrates an electron bunch 40 riding an electromagnetic wave 42 at three different regions in an accelerator structure of a TW LINAC. FIG. 9 illustrates a lower energy operation of the LINAC. The electron bunch is depicted in FIG. 9 as substantially non-synchronous. The phase velocity of the electromagnetic wave has been adjusted such that the phase velocity is slower than the speed of the electron bunches (e.g., by increasing the RF frequency of the electromagnetic wave). In this lower energy beam operation, the electromagnetic fields can be smaller and the electron beam can be accelerated more slowly in the buncher region. When the electron bunch leaves the buncher region of the accelerator structure, it can be behind the crest of the electromagnetic wave. At approximately the middle of the accelerator structure, the electron bunch 40 is at the crest of the electromagnetic wave 42. At the end of the accelerator structure, the electron bunch 40 is ahead of the crest of the electromagnetic wave 42. On average, the electron bunch 40 is at the crest of the electromagnetic wave 42. Therefore, the electron bunch has an energy spectrum that is equivalent to an electron bunch that rides at the crest of a smaller amplitude electromagnetic wave throughout the accelerator structure. As a result, jitter does not cause a significant change in energy of the electron beam, and thus of a resulting X-ray beam.

In one embodiment, the phase velocity is adjusted so that the bunch is as far ahead of the crest at the end of the accelerator structure as it was behind the crest at the end of the buncher region of the accelerator structure for a given energy level. That way the electrons at the head of the bunch that gained more energy in the first half of the accelerator structure than the electrons at the tail of the bunch can gain less energy in the second half of the accelerator structure, and the two effects cancel to first order. Similarly, if the RF frequency jitters by a tiny amount causing the electron bunch to be farther behind at the beginning so that it gains less energy in the first half of the accelerator, it gains more energy in the second half, thus minimizing the energy jitter. The net effect of adjusting the frequency in this way is to make the energy distribution within the bunch at the end of the accelerator structure look as if the bunch rode on the crest of a smaller amplitude wave throughout the accelerator. This adjustment of the frequency can also maximize the energy gain (provide maximum X-ray yield) for the particular amplitude of the electromagnetic waves and reduce beam energy dependence on RF power level.

In another embodiment, the phase velocity is adjusted so that the bunch is further ahead of the crest at the end of the accelerator structure than it was behind the crest at the beginning of the accelerator structure for a given energy level. In other words, the RF frequency is raised to above the point where maximum X-ray yield can be obtained. Such an adjustment can address amplitude jitter introduced into the accelerating fields of the LINAC based on amplitude jitter in the RF source. It should be noted, however, that such an adjustment can cause a wider energy spectrum of the electron beam and the X-rays than adjusting the phase velocity so that the bunch is as far ahead of the crest at the end of the accelerator structure as it was behind the crest at the beginning of the accelerator structure for a given energy level.

As discussed above, frequency jitter from the RF source, temperature variation from the accelerator structure and amplitude jitter from the RF source all cause the electron bunch to move off the peak of the electromagnetic wave. However, amplitude jitter in the RF source also causes jitter in the amplitude of the accelerating fields throughout the LINAC. When the phase velocity (e.g., RF frequency) is adjusted to place the bunch, on average, ahead of the peak of the electromagnetic wave, the jitter in the amplitude of the accelerating fields can be ameliorated. The amplitude of the RF source can also be adjusted to ameliorate the amplitude jitter. Alternatively, or in addition, the pulse repetition rate of the LINAC can be changed to ameliorate the sources of jitter. For example, where there is a 180 Hz or 360 Hz ripple experienced by the TW LINAC when operating at 6 MeV, the pulse repetition rate can be changed from 400 pulses per second (pps) to 360 pps to alleviate jitter.

The jitter in the X-ray yield can be strikingly reduced by raising the RF frequency above the point where the maximum X-ray yield is obtained. This is optimum because when the frequency is raised above the maximum X-ray yield point it reduces the phase velocity of the electromagnetic wave and moves the bunch ahead of the accelerating crest on average in the LINAC. Then, if the RF amplitude jitters upward, the bunch moves farther ahead of the crest and the downward slope of the sine wave compensates for the increase in the accelerating fields in the LINAC. At some frequency the derivative of beam energy or X-ray yield with respect to RF power actually vanishes.

In one embodiment, the optimum RF frequency depends on the relative amplitude of the three sources of X-ray yield jitter. If the bunch is moved forward of the accelerating crest by just increasing the RF frequency, the beam energy and the X-ray yield will decrease. However, the bunch can be moved forward of the accelerator crest by increasing both the frequency and the amplitude of the RF drive, in a manner which keeps the energy approximately constant. In one embodiment, in the commissioning of a LINAC system, when a beam energy spectrometer is available, the function of power versus RF frequency above the maximum X-ray yield point, for each operating energy, is measured. Then an operator can find the point along this power versus frequency curve which gives the best stability and operate there.

The ability to change the phase velocity of the wave by just changing the frequency (or by changing the frequency and amplitude) enables the electron bunch to be at an optimum position relative to an electromagnetic wave for a given energy level. Therefore, stable X-rays can be generated at a range of energy levels. This causes the TW LINAC to be less susceptible to temperature changes, less susceptible to jitter in the frequency of the electromagnetic wave, and less susceptible to jitter in the amplitude of the electromagnetic wave.

Use of a Frequency Controller in the Operation of a Multi-Energy TW LINAC

In a multi-energy interleaving operation of a TW LINAC, a frequency controller can be used to measure the phase shift of the electromagnetic wave through the LINAC structure by comparing the phase of the electromagnetic wave at the input of the accelerator structure to the phase of the electromagnetic wave at the output of the accelerator structure. The frequency controller can transmit a signal to the oscillator to modify the frequency of the electromagnetic wave that is ultimately coupled into the accelerator structure based on the magnitude of the phase shift detected by the frequency controller. In a non-limiting example, the frequency controller can be an automatic frequency controller (AFC). The frequency controller can be a multi-frequency AFC, and can operate at a set point for each of several different frequencies, with each frequency being associated with each different energy. The frequency controller can be used to measure the RF phase of the electromagnetic wave at the output coupler relative to the RF phase of the electromagnetic wave at the input coupler. With this information, the frequency controller can be used to the frequency of the electromagnetic wave, to maintain the phase shift through the LINAC to a separate set point for each of the different energies of operation of the LINAC. The frequency controller can facilitate stable operation with quick settling during rapid switching of a multi-energy interleaved TW LINAC. For example, the frequency controller can be used to correct for the effect of rapid thermalization of the TW LINAC accelerator structure when the system is stepping from standby to full power, drifts in the temperature of the accelerator structure cooling water, or drifts in the frequency of the oscillator.

Figure 10:
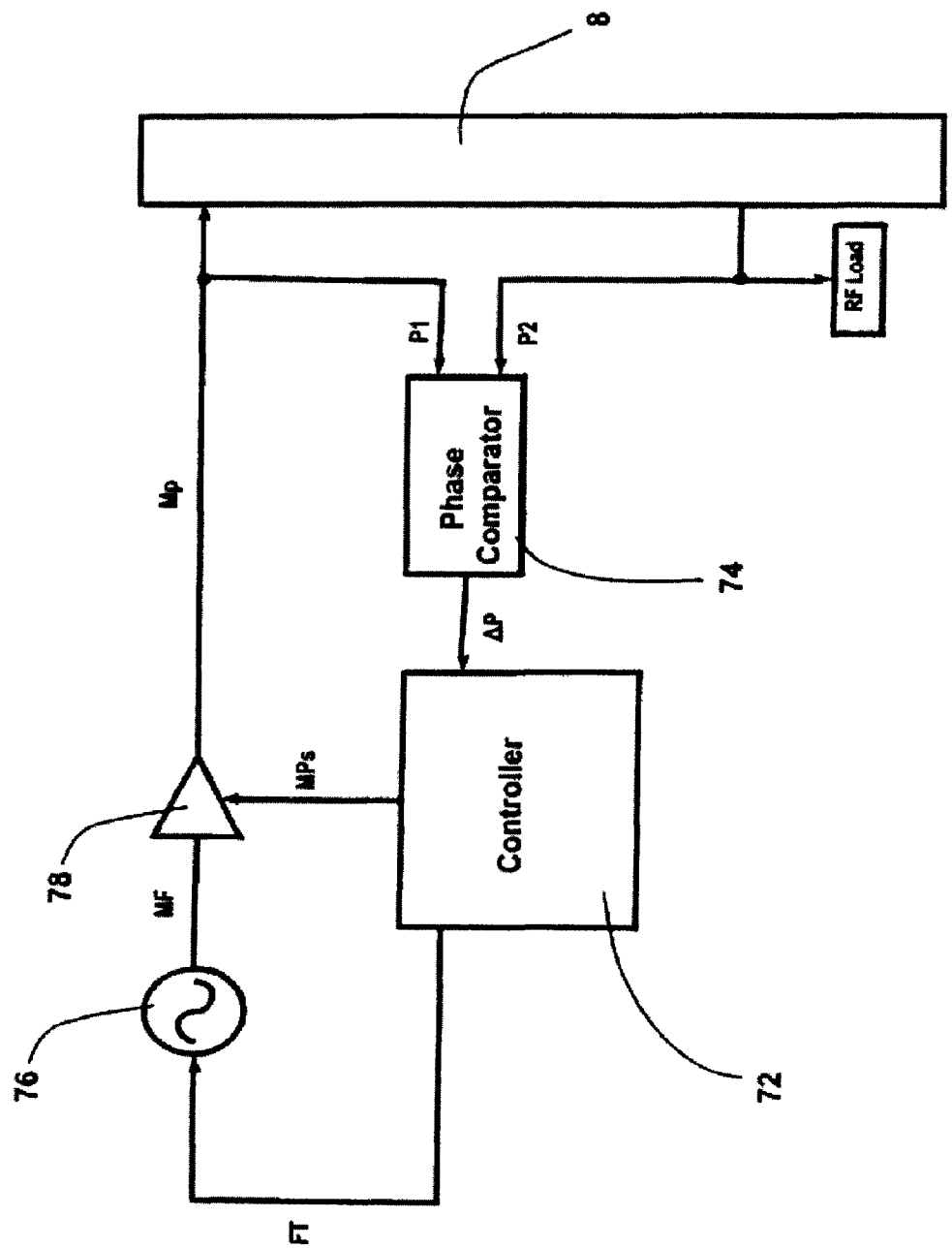
FIG. 10 illustrates a block diagram of a TW LINAC comprising a frequency controller.

FIG. 10 shows a block diagram of an embodiment of a TW LINAC comprising a frequency controller. In the illustration of FIG. 10, the frequency controller comprises a controller 72 and a phase comparator 74. In the example of FIG. 10, the phase comparator 74 compares the electromagnetic wave at the input of the accelerator structure 8 (P1) and at the output of the accelerator structure 8 (P2) and provides a measure of the phase shift ($\Delta P$) to the controller 72. The frequency controller can transmit a signal to the oscillator 76 to tune the frequency of the oscillator 76. As discussed above, the oscillator 76 can generate a signal having a frequency that is provided by the frequency controller, and the RF signal can be amplified by the amplifier 78 and supplied to a klystron (not shown). Thus, the signal from the frequency controller to the oscillator 76 can ultimately result in a modification of the frequency of the electromagnetic wave that is coupled into the accelerator structure, based on the magnitude of the phase shift detected by the frequency controller. The oscillator 76 can also generate a signal that results in a change of the frequency of the electromagnetic wave by an amount to change the operating energy of the LINAC in the tome interval between electromagnetic wave pulses an interleaving operation. The frequency controller is illustrated in FIG. 10 as comprising a controller 72 and a phase comparator 74 as separate units. However, in other embodiments, the frequency controller can comprise the controller and phase comparator as an integral unit.

Figure 11:
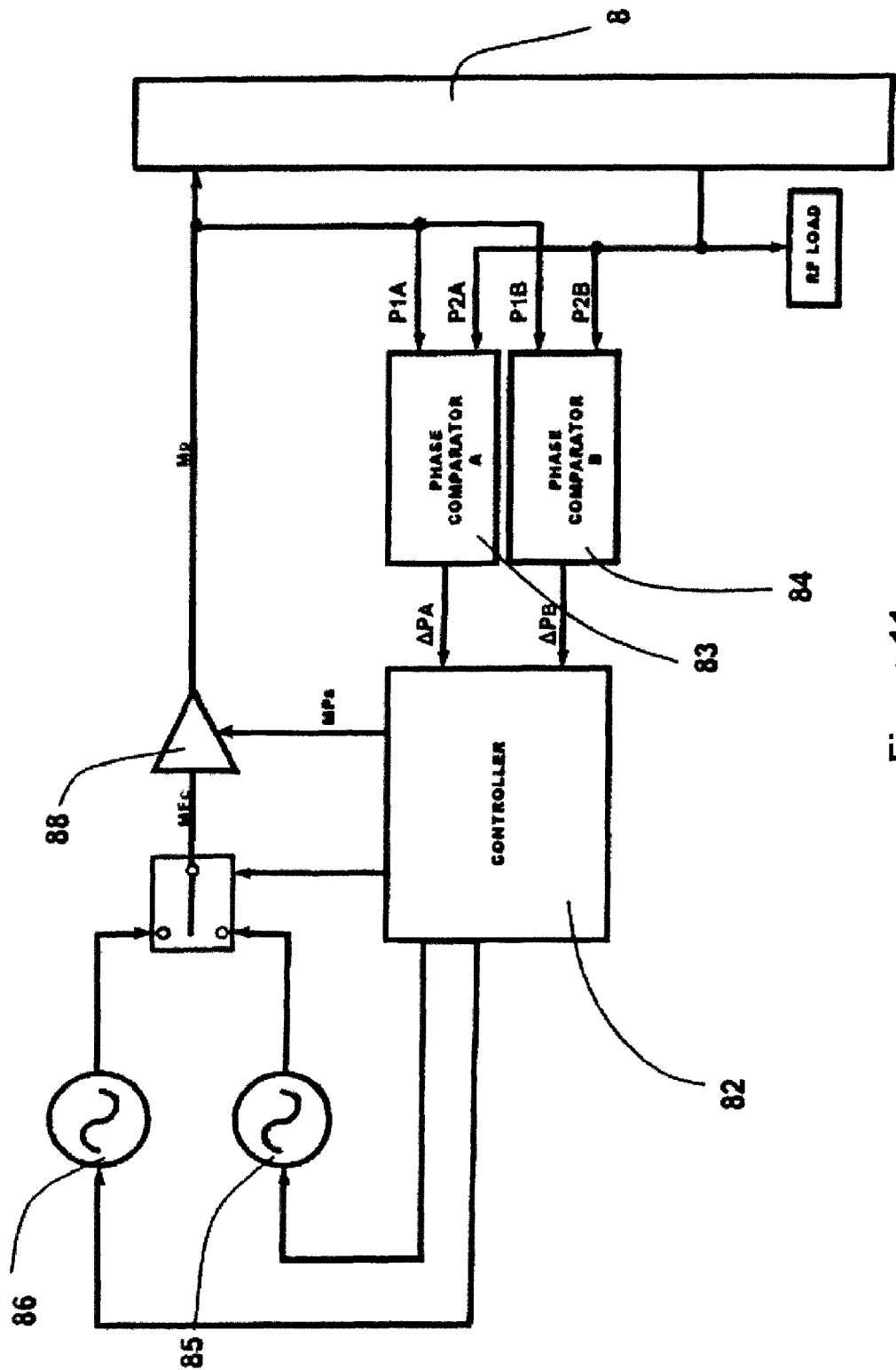
FIG. 11 illustrates another block diagram of a TW LINAC comprising a frequency controller.

FIG. 11 shows a block diagram of another embodiment of a TW LINAC comprising a frequency controller that can be used for a dual energy operation. In the illustration of FIG. 11, the frequency controller comprises a controller 82, and two phase comparators (phase comparator A 83 and phase comparator B 84) that are each used for a different energy of operation of the LINAC. Phase comparator A 83 compares the electromagnetic wave at the input of the accelerator structure 8 (P1A) and at the output of the accelerator structure 8 (P2A) and provides a measure of the phase shift (ΔPA) to the controller 82. Phase comparator B 84 compares the electromagnetic wave at the input of the accelerator structure 8 (P1B) and at the output of the accelerator structure 8 (P2B) and provides a measure of the phase shift (ΔPB) to the controller 82. The illustration of FIG. 11 includes two oscillators (oscillator 85 and oscillator 86), each used for a different energy of operation of the LINAC. Frequency controller 82 can transmit a signal to oscillator 85 to tune the frequency of oscillator 85 based on the measured phase shift ΔPA of an electromagnetic wave used to accelerate a set of electrons to the desired first energy of operation. In addition, frequency controller 82 can also transmit a signal to oscillator 86 to tune the frequency of oscillator 86 based on the measured phase shift ΔPB of an electromagnetic wave used to accelerate a set of electrons to the desired second energy of operation. As discussed above, oscillators 85 and 86 can each generate an RF signal having a frequency that is provided by the frequency controller, and the RF signal can be amplified by amplifier 88 and supplied to a klystron (not shown). Thus, the signal from the frequency controller to oscillator 85 (or oscillator 86) can ultimately result in a modification of the frequency of the electromagnetic wave that is coupled into the accelerator structure, for a given energy of operation, based on the magnitude of a phase shift detected by the frequency controller. The frequency controller is illustrated in FIG. 11 as comprising a controller 82, phase comparator A 83, and phase comparator B 84 as separate units. However, in other embodiments, the frequency controller can comprise the controller and the phase comparators as an integral unit.

Figure 12:
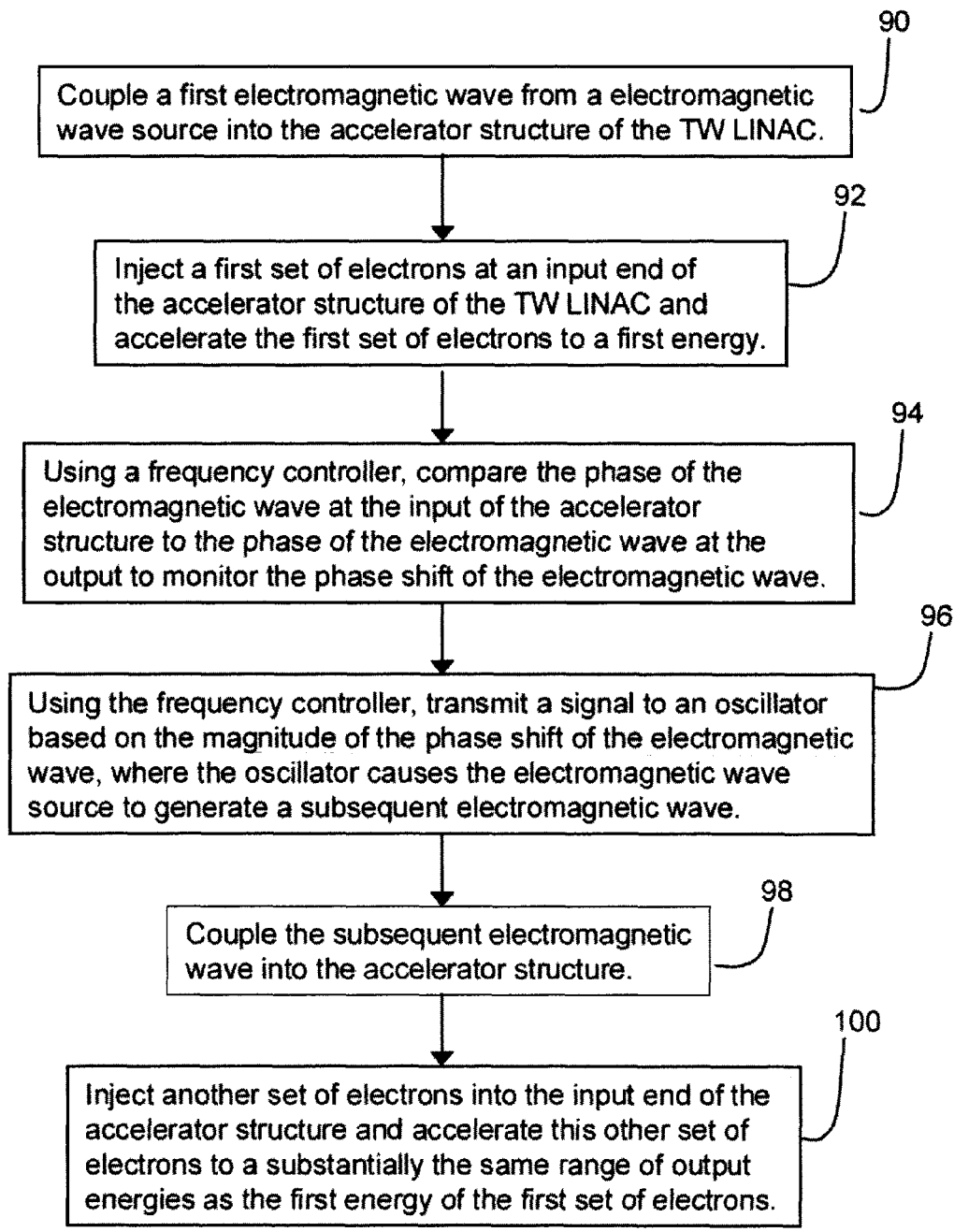
FIG. 12 shows a flow chart of an operation of a TW LINAC comprising a frequency controller.

FIG. 12 shows a flow chart of steps in an example operation of the TW LINAC. In step 90 of FIG. 12, a first electromagnetic wave from an electromagnetic wave source is coupled into the accelerator structure of the TW LINAC. In step 92, a first set of electrons is injected at the input of the accelerator structure of the TW LINAC and the first set of electrons is accelerated to a first energy. In step 94, a frequency controller compares the phase of the electromagnetic wave at the input of the accelerator structure to the phase of the electromagnetic wave at the output to monitor the phase shift of the electromagnetic wave. Step 94 can occur during the acceleration of the first set of electrons to a first energy in step 92. In step 96, the frequency controller transmits a signal to an oscillator, and the oscillator can cause the electromagnetic wave source to generate a subsequent electromagnetic wave at a corrected frequency based on the magnitude of the phase shift detected by the frequency controller. For example, the corrected frequency can differ from the first frequency by an amount δf based on magnitude of the phase shift detected (for example, δf can be a difference on the order of about 0.000001 MHz or more, about 0.00001 MHz or more, about 0.001 MHz or more, about 0.01 MHz or more, about 0.03 MHz or more, about 0.05 MHz or more, about 0.08 MHz or more, about 0.1 MHz or more, or about 0.15 MHz or more). The subsequent electromagnetic wave of step 98 has about the same amplitude as the electromagnetic wave of step 90. For example, these electromagnetic waves can have about the same magnitude if they differ by less than about 0.1%, less than about 1%, less that about 2%, less than about 5% in magnitude, less than about 10% in magnitude, or more. As discussed above, the oscillator can generate a signal having a frequency that is provided by the frequency controller, and that signal can be amplified by an amplifier and supplied to the electromagnetic wave source (such as a klystron). The electromagnetic wave source can generate the subsequent electromagnetic wave based on the amplified signal received from the amplifier.

In step 98, the subsequent electromagnetic wave is coupled into the accelerator structure. In step 100, another set of electrons is injected at the input of the accelerator structure of the TW LINAC and this set of electrons is accelerated by the subsequent electromagnetic wave to substantially the same range of output energies as the first energy of the first set of electrons. The range of output energies of two different sets of electrons is substantially the same if the central value (e.g., the mean value or median value) of the range of output energies differs by less than about 0.1%, less than about 1%, less that about 2%, less than about 5% in magnitude, less than about 10% in magnitude, or more. Steps 90-100 can be repeated a number of times during operation of the TW LINAC.

In an interleaving operation, the LINAC can be operated to cycle between two different output energies. For example, the LINAC can be operated to alternate between about 6 MeV and about 9 MeV. In such an operation, after step 96 but prior to step 98, the LINAC can be operated at an energy (for example, about 9 MeV) that is different from the first energy of the first set of electrons (for example, about 6 MeV). The amplitude and frequency in the accelerator structure of the electromagnetic wave used for accelerating these additional electrons can be different than the electromagnetic wave used in step 90. For example, in the interleaving operation, a first electromagnetic wave is generated and used to accelerate a first set of electrons to the first energy, a second electromagnetic wave (of a different amplitude and frequency) is generated and used to accelerate a second set of electrons to a second energy that is different from the first energy, then a subsequent electromagnetic wave is generated based on the phase shift of the first electromagnetic wave (as discussed above) and used to accelerate a subsequent set of electrons to substantially the same range of energies as the first energy. In yet another example of an interleaving operation, the LINAC is operated for multiple pulses at the first energy before it is operated at the second energy. The LINAC can also be operated to provide multiple pulses at the first energy and then operated to provide multiple pulses at the second energy.

In another example operation, prior to step 90, a phase set point for the first energy can be input into the phase comparator. The phase shift can be inserted into one input arm of the phase comparator so that the phase comparator outputs a reading of, e.g., zero voltage, when the phase is correct for the desired energy of the pulse. In another example, after step 94 and prior to step 96, a phase set point for the second energy can be input into the phase comparator.

The frequency controller can have several different set points for the optimum phase shift for each of the different energies at which the TW LINAC is operated. For example, the frequency controller can have N different set points for the optimum phase shift that corresponds to each of N different energies (N≧2) at which the TW LINAC is operated.

The frequency controller can perform the phase comparison continuously as a beam of electrons is accelerated in the accelerator structure. For example, frequency controller can perform the phase comparison continuously from the moment an electromagnetic wave is coupled into the input of the accelerator structure until the electrons are output from the output of the accelerator structure. The set point for the phase bridge can be changed before another electromagnetic wave is coupled into the accelerator structure, so that the set point is appropriate for the intended energy range of the subsequent pulse of output electrons.

The frequency controller can adjust the frequency to achieve the desired phase set point. For example, for a TW LINAC in which the accelerator structure is a forward wave structure, the frequency controller can transmit a signal to result in the raising of the frequency for the lower energy operation in which the electron beam is moving slower through the buncher region. In another example, for a TW LINAC in which the accelerator structure is a forward wave structure, the frequency controller can transmit a signal to result in the lowering of the frequency for the higher energy operation in which the electron beam is moving faster through the buncher region. The transit time of the electron beam through the buncher region can differ greatly from the lower energy operation to the higher energy operation when the electrons are being accelerated from, e.g., about 15 keV (an example energy of electrons emerging from an electron gun) to about 1 MeV. The difference in transit times results from the different electric field amplitudes being applied to the electrons for the lower energy beam versus the higher energy beam. For example, electric field amplitudes used for the lower energy beam can be about $\frac{2}{3}$ as high as that used for the higher energy beam in a dual-energy operation. The frequency controller can transmit a signal to result in the adjustment of the frequency of the electromagnetic wave to make the transit time of the electromagnetic wave crests through the structure optimized for the transit time of the electrons through the accelerator structure for each of the different energies in the interleaved operation of the TW LINAC. For example, frequency controller can transmit a signal to provide electromagnetic wave crests whose transit time through the accelerator structure is longer for lower energy electron beams.

In examples where the accelerator structure is a backward wave structure, the sign of the frequency change in the foregoing discussions would be reversed. For example, if the frequency is raised to achieve a result for a forward wave structure, it is lowered to achieve that result for a backward wave structure.

Changing the frequency of the electromagnetic wave can change the phase velocity of the wave so that, at each electron beam energy, the electron bunch can be on the average on the crest of the wave. The TW LINAC can be configured so that, for one particular energy, termed the synchronous energy, the buncher region and the accelerating structure of the LINAC can be designed so that the bunch is near the crest all the way through the LINAC. If the TW LINAC is to be operated over a large energy range, e.g., energies ranging from 3 MeV to 9 MeV, the synchronous energy can be chosen to be near the middle of the operating range.

If the input power (and hence amplitude) of the electromagnetic wave is lowered to lower the fields, and thus lower the energy of the electron beam, the fields can decrease uniformly throughout the LINAC. However, the effect of the decrease in power of the electromagnetic wave (including decreased electron velocity) can be more concentrated in the buncher region, since the velocity of the electrons becomes considerably less sensitive to the power of the electromagnetic wave once the electrons approach relativistic speeds. A change in phase velocity of the wave resulting from a change in frequency for a constant gradient forward wave TW LINAC can be small at the input end of the accelerator structure and large at the output end. The frequency controller can transmit a signal to change the frequency of an electromagnetic wave such that the electron bunch travels substantially behind the crest in the first third of the accelerator structure, to reach the crest by around the middle of the accelerator structure, and to be substantially ahead of the crest in the last third of the accelerator structure. In this example, the energy correlation as a function of position within the electron bunch that the electrons gain in the first third of their travel through the LINAC can be removed by traveling ahead of the crest in the last third of their travel through the LINAC. The frequency adjustment that removes the energy correlation as a function of position can also maximize the energy gain through the LINAC, and can maximize the X-ray yield.

For a given energy of operation, the optimum frequency and the set point of the frequency controller can be functions of both the energy and the beam current from the electron gun. The beam current from the electron gun can be varied to change the output energy of the electrons through the beam loading effect. In the beam loading effect, the electron beam bunched at the operating frequency of the LINAC can induce a field in the accelerator structure that has a phase that opposes the acceleration applied by the electromagnetic wave coupled into the LINAC, and can act to oppose the forward motion of the electrons. That is, beam loading can induce fields that act to decelerate the electron beam. The amplitude of these induced fields vary linearly with the magnitude of the beam current, and can rise roughly linearly with distance along the accelerator structure. A higher electron beam current can induce electric fields of higher amplitude that oppose the acceleration applied by the electromagnetic wave coupled into the LINAC, and result in the electron beam experiencing less acceleration. In effect, beam loading can decrease the amplitude of the electromagnetic wave. A desirable result of increasing the electron gun current (and hence the effect of beam loading) to lower the energy of the output electrons can be that the X-ray yield can be increased, for example, from the increased dose rate of electrons.

The beam loading effect can lower the energy of the electron beam, while having little effect on the transit time of the electron beam through the accelerator, since the electron beam induced fields are small at the input end where the electron beam is non-relativistic. If the power of the electromagnetic wave is raised in an effort to compensate for the lowered energy that can result from beam loading, the fields can change equally in all cavities of the accelerator structure and have a strong effect on the beam transit time through the accelerator structure. Thus, for each different energy in an interleaving operation, an adjustment in the set point of the frequency controller can be made to account for the different RF phase shifts through the LINAC that can occur for each different energy of operation, for example, due to the effect of beam loading.

In a multi-energy operation of the LINAC, the electron gun can be operated at a different beam current for each energy of operation. As discussed above, increasing the beam current for the lower energy operation can provide an increased X-ray yield at the lower energy than achieved by just lowering the amplitude of the electromagnetic wave from the klystron. Using a different beam current from the electron gun for each different energy of operation of the LINAC can help maintain the same X-ray intensity across the different energies of operation.

In another embodiment, an operator can choose a phase shift through the LINAC for each different energy which maximizes the X-ray yield for that energy. That is, an operator can choose the set point of the frequency controller for each different energy of operation. The frequency controller can then continuously adjust the frequency of the electromagnetic wave to maintain the phase of the electromagnetic wave at the preset phase set point for that energy. It appears that a similar value of phase shift through the LINAC can optimize the electron spectrum (i.e., eliminate the energy correlation with position in the bunch along the longitudinal direction of the LINAC), maximize the energy, and maximize the X-ray yield. However, maximizing the X-ray yield can be sensitive to frequency and can be easy to perform.

In an embodiment, the frequency controller can maintain automatic control over the adjustments to the frequency of the electromagnetic wave in a feedback operation. In a non-limiting example, the frequency controller can be an automatic frequency controller (AFC).

In another embodiment, a frequency controller can maintain automatic control and adjust the frequency of the electromagnetic wave to stabilize the energy of the electrons output at a given energy of operation. The energy of the electrons are stabilized when the energy spectrum of the electrons is centered at or substantially near the desired energy of operation of the accelerator (i.e., the maximum attainable energy of the LINAC for the given electromagnetic fields), and the full-width at half-maximum of the energy spectrum of the output electrons is minimized (i.e., narrowed). All of the systems and methods disclosed herein are also applicable to this embodiment of the operation of the TW LINAC comprising the frequency controller. For example, the frequency controller can maintain automatic control and adjust the frequency of the electromagnetic wave to stabilize the energy of the electrons at each energy of operation. In this example, the frequency controller can compare a first output of electrons at an energy to a second output of electrons at that same energy, and frequency controller transmits a signal to an oscillator, and adjust the frequency of the electromagnetic wave to stabilize the output of electrons. The frequency of the electromagnetic wave can be varied on alternate pulses of the same energy to determine the behavior of the measured output of electrons versus frequency, and thus determine the change in frequency that can cause the output of electrons to peak around the desired energy, with minimized energy spread.

In another embodiment, the frequency controller can maintain automatic control and adjust the frequency of the electromagnetic wave to maximize the yield of X-rays at each energy (generated by contacting a target with the output electrons). For example, the frequency controller can transmit a signal to adjust the frequency of the electromagnetic wave based on the measured yield of X-rays. The maximum of the yield of X-rays at a given energy of the interleaving operation can be predetermined. The frequency of the electromagnetic wave can be varied on alternate pulses of the same energy to determine the behavior of the measured yield of X-rays versus frequency, and thus determine the change in frequency that can cause the yield to move towards the maximum. In this example, the yield of X-rays on two successive pulses at the same energy can be compared to determine the adjustment to the electromagnetic wave frequency. In a specific embodiment, the frequency can be varied by about 100 kHz on alternate pulses of the same energy, resulting in a change in phase through the structure of about 8 degrees of phase. With this frequency variation, the electron bunch can alternate between about 2 degrees forward and about 2 degrees behind the crest of the electromagnetic wave on successive pulses of the same energy.

The frequency controller can maintain automatic control over the adjustments to the frequency of the electromagnetic wave in a feedback operation. A feedback loop can be intricate and the convergence time to determine a frequency adjustment can be long. The convergence time can be reduced by making the frequency correction (or adjustment) proportional to the error signal. In the embodiment where the frequency controller is used to maximize the yield of X-rays at each energy of operation, the error signal can be determined as the difference between the X-ray yield from two pulses, divided by the sum of the X-ray yields from the two pulses. The energy of the beam can be approximated as a sine function of phase shift through the LINAC. Normalizing by the sum of the two X-ray yields can cause the error signal measure to be insensitive to changes in the X-ray measurement device. In the embodiment where the frequency controller is used to stabilize the energy of the output electrons at each energy of operation, the error signal can be determined as the difference between the electron current from two pulses, divided by the sum of the electron currents from the two pulses.

A frequency controller operated in a feedback operation can be used to correct for the effect of minor drifts of the electron gun current or minor drifts of the RF power (hence amplitude). That is, in addition to correcting for drifts in the temperature of the accelerator structure or drifts in the frequency of the oscillator.

X-Rays

In certain aspects, X-rays can be generated from the bombardment of a target material by the accelerated electron beam or electron bunches from a LINAC. The X-rays can be generated by two different mechanisms. In the first mechanisms, collision of the electrons from the LINAC an atom of a target can impart enough energy so that electrons from the atom's lower energy levels (inner shell) escape the atom, leaving vacancies in the lower energy levels. Electrons in the higher energy levels of the atom descend to the lower energy level to fill the vacancies, and emit their excess energy as X-ray photons. Since the energy difference between the higher energy level and the lower energy level is a discrete value, these X-ray photons (generally referred to as k-shell radiation) appear in the X-ray spectrum as sharp lines (called characteristic lines). K-shell radiation has a signature energy that depends on the target material. In the second mechanisms, the electron beams or bunches from the LINAC are scattered by the strong electric field near the atoms of the target and give off Bremsstrahlung radiation. Bremsstrahlung radiation produces X-rays photons in a continuous spectrum, where the intensity of the X-rays increases from zero at the energy of the incident electrons. That is, the highest energy X-ray that can be produced by the electrons from a LINAC is the highest energy of the electrons when they are emitted from the LINAC. The Bremsstrahlung radiation can be of more interest than the characteristic lines for many applications.

Materials useful as targets for generating X-rays include tungsten, certain tungsten alloys (such as but not limited to tungsten carbide, or tungsten (95%)-rhenium (5%)), molybdenum, copper, platinum and cobalt.

Instrumentation

Certain instruments which may be used in the operation of a traveling wave LINAC include a klystron modulator and an electromagnetic wave source.

Modulator

A modulator generates high-voltage pulses lasting a few microseconds. These high-voltage pulses can be supplied to the electromagnetic wave source (discussed below), to the electron gun (see above), or to both simultaneously. A power supply provides DC voltage to the modulator, which converts this to the high-voltage pulses. For example, the Solid State Klystron Modulator-K1 or -K2 (ScandiNova Systems AB, Uppsala, Sweden) can be used in connection with a klystron.

Microwave Generators

The electromagnetic wave source can be any electromagnetic wave source deemed suitable by one of skill. The electromagnetic wave source (in the microwave of radio frequency ("RF") range) for the LINAC can be a klystron amplifier (discussed above). In a klystron, the size of the RF source and the power output capability are roughly proportional to the wavelength of the electromagnetic wave. The electromagnetic wave can be modified by changing its amplitude, frequency, or phase.

Exemplary Apparatus and Computer-Program Implementations

Aspects of the methods disclosed herein can be performed using a computer system, such as the computer system described in this section, according to the following programs and methods. For example, such a computer system can store and issue commands to facilitate modification of the electromagnetic wave frequency according to a method disclosed herein. In another example, a computer system can store and issue commands to facilitate operation of the frequency controller according to a method disclosed herein. The systems and methods may be implemented on various types of computer architectures, such as for example on a single general purpose computer, or a parallel processing computer system, or a workstation, or on a networked system (e.g., a client-server configuration such as shown in FIG. 13).

Figure 13:
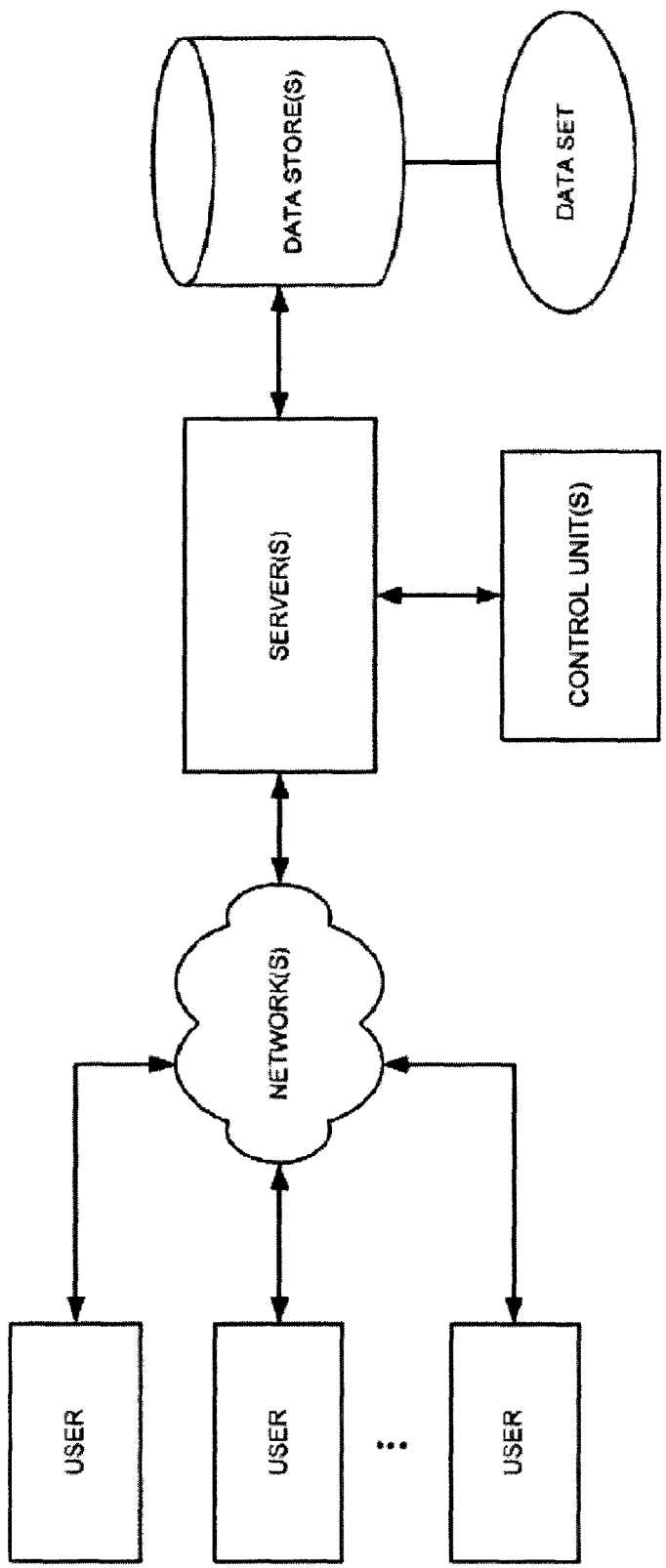
FIG. 13 shows a block diagram of an example computer structure for use in the operation of a TW LINAC comprising a frequency controller.

An exemplary computer system suitable for implementing the methods disclosed herein is illustrated in FIG. 13. As shown in FIG. 13, the computer system to implement one or more methods and systems disclosed herein can be linked to a network link which can be, e.g., part of a local area network ("LAN") to other, local computer systems and/or part of a wide area network ("WAN"), such as the Internet, that is connected to other, remote computer systems. A software component can include programs that cause one or more processors to issue commands to one or more control units, which cause the one or more control units to issue commands to cause the initiation of the frequency controller, to operate the electromagnetic wave source to generate an electromagnetic wave at a frequency, and/or to operate the LINAC (including commands for coupling the electromagnetic wave into the LINAC). The programs can cause the system to retrieve commands for executing the steps of the methods in specified sequences, including initiating the frequency controller and operating the electromagnetic wave source to generate an electromagnetic wave at a frequency, from a data store (e.g., a database). Such a data store can be stored on a mass storage (e.g., a hard drive) or other computer readable medium and loaded into the memory of the computer, or the data store can be accessed by the computer system by means of the network.

While various illustrative embodiments of the invention are described above, it will be apparent to one skilled in the art that various changes and modifications may be made therein without departing from the invention. For example, although the embodiments above have been described primarily with respect to inspecting cargo containers, it should be appreciated that the systems and methods suitably may be modified to inspect materials in any desired context, including inside of vehicles, rail cars, and the like. The appended claims are intended to cover all such changes and modifications that fall within the true spirit and scope of the invention.

What is claimed:

1. A system for interrogating an object, the system comprising:
   a single linear accelerator configured to generate first and second electron beams respectively having first and second energies;
   first and second targets;
   a magnet configured to control irradiation of the first and second targets by the first and second electron beams; and
   a controller in operable communication with the linear accelerator and with the magnet, the controller configured to:
   (a) cause the linear accelerator to generate the first electron beam at a first time and cause the magnet to direct the first electron beam to the first target so as to generate a first X-ray beam that has a first X-ray energy and irradiates the object; and
   (b) cause the linear accelerator to generate the second electron beam at a second time and cause the magnet to direct the second electron beam to the second target so as to generate a neutron beam that irradiates the object.

2. The system of claim 1, wherein the magnet is configured to deflect the second electron beam to irradiate the second target responsive to a control signal from the controller.

3. The system of claim 2, wherein the magnet is configured to allow the first electron beam to irradiate the first target without deflection responsive to a control signal from the controller.

4. The system of claim 1, wherein the controller is configured to interleave the first X-ray beam and the neutron beam by repeating (a) and (b).

5. The system of claim 1, further comprising an X-ray detector configured to detect a percent transmission of the first X-ray beam through the object.

6. The system of claim 5, wherein the controller is in operable communication with the detector and is configured to perform (b) when the percent transmission is less than a predetermined threshold.

7. The system of claim 1, wherein the linear accelerator is further configured to generate a third electron beam having a third energy, and wherein the controller is further configured to (c) cause the linear accelerator to generate the third electron beam at a third time and cause the magnet to direct the third electron beam to the first target so as to generate a second X-ray beam that has a second X-ray energy and irradiates the object.

8. The system of claim 7, wherein the controller is configured to interleave the first and second X-ray beams and the neutron beam by repeating (a), (b), and (c).

9. The system of claim 7, further comprising an X-ray detector configured to detect percent transmissions of the first and second X-ray beams through the object.

10. The system of claim 9, wherein the controller is in operable communication with the detector and is configured to perform (b) when the percent transmissions are less than a predetermined threshold.

11. The system of claim 1, wherein the linear accelerator and the first and second targets all share a common vacuum.

12. The system of claim 1, wherein the controller is further configured to select a dose of the first X-ray beam by selecting one of a beam current and a pulse width of the first electron beam, and to select a dose of the neutron beam by selecting one of a beam current and a pulse width of the second electron beam.

13. The system of claim 1, wherein the first and second energies are different from one another.

14. A method of interrogating an object, the method comprising:
- generating with a single linear accelerator first and second electron beams respectively having first and second energies;
- directing the first electron beam to a first target so as to generate a first X-ray beam having a first X-ray energy at a first time;
- irradiating the object with the first X-ray beam;
- directing the second electron beam to a second target so as to generate a neutron beam at a second time; and
- irradiating the object with the neutron beam.

15. The method of claim 14, wherein directing the second electron beam to the second target comprises deflecting the second electron beam with a magnet.

16. The method of claim 15, wherein directing the first electron beam to the first target comprises allowing the first electron beam to travel undeflected from the single linear accelerator to the first target.

17. The method of claim 16, comprising interleaving the first and second electron beams and directing the first and second electron beams to the first and second targets in synchrony with the interleaving.

18. The method of claim 15, wherein the first and second energies are different from one another.

19. The method of claim 14, further comprising detecting a percent transmission of the first X-ray beam through the object.

20. The method of claim 19, wherein the second electron beam is generated and directed to the target when the detected percent transmission is less than a predetermined threshold.

21. The method of claim 14, further comprising:
- generating with the single linear accelerator a third electron beam having a third energy;
- directing the third electron beam to the first target so as to generate a second X-ray beam having a second X-ray energy; and
- irradiating the object at a third time with the second X-ray beam.

22. The method of claim 21, further comprising interleaving the first, second, and third electron beams generated by the single linear accelerator and controlling direction of the first, second, and third electron beams to the first and second targets in synchrony with the interleaving.

23. The method of claim 21, further comprising detecting a percent transmission of the first and second X-ray beams through the object.

24. The method of claim 23, wherein the second electron beam is generated and directed to the second target when the percent transmission less than a predetermined threshold.

25. The method of claim 14, wherein the linear accelerator and the first and second targets all share a common vacuum.

26. The method of claim 14, further comprising selecting a dose of the first X-ray beam by selecting one of a beam current and a pulse width of the first electron beam, and selecting a dose of the neutron beam by selecting one of a beam current and a pulse width of the second electron beam.

\* \* \* \* \*